(12) United States Patent
Kannenberg et al.

(10) Patent No.: US 6,939,346 B2
(45) Date of Patent: Sep. 6, 2005

(54) METHOD AND APPARATUS FOR CONTROLLING A TEMPERATURE-CONTROLLED PROBE

(75) Inventors: Donald P. Kannenberg, San Jose, CA (US); Duane W. Marion, Danville, CA (US)

(73) Assignee: Oratec Interventions, Inc., Menlo Park, CA (US)

( * ) Notice: Subject to any disclaimer, the term of this patent is extended or adjusted under 35 U.S.C. 154(b) by 0 days.

(21) Appl. No.: 10/187,462

(22) Filed: Jun. 28, 2002

(65) Prior Publication Data

US 2003/0060818 A1 Mar. 27, 2003

Related U.S. Application Data

(63) Continuation-in-part of application No. 09/738,944, filed on Dec. 14, 2000, now abandoned, which is a continuation of application No. 09/296,690, filed on Apr. 21, 1999, now Pat. No. 6,162,217.

(51) Int. Cl.[7] .............................................. A61B 18/04
(52) U.S. Cl. .......................................... 606/34; 608/38
(58) Field of Search ................... 606/34, 38, 40–42, 606/49–50; 607/101–105

(56) References Cited

U.S. PATENT DOCUMENTS

| | | | |
|---|---|---|---|
| 164,184 A | 6/1875 | Kidder | |
| 300,155 A | 6/1884 | Starr | |
| 371,664 A | 10/1887 | Brannan et al. | |
| 452,220 A | 5/1891 | Gunning | |
| 1,314,855 A | 9/1919 | Carpenter | |
| 1,366,756 A | 1/1921 | Wappler | |
| 1,731,627 A | 10/1929 | Johnson et al. | |
| 1,735,271 A | 11/1929 | Groff | |
| 1,814,791 A | 7/1931 | Ende | |

(Continued)

FOREIGN PATENT DOCUMENTS

| | | |
|---|---|---|
| EP | 0558297 A2 | 9/1993 |
| GB | 2160102 A | 12/1985 |
| WO | PCT/US93/10467 | 5/1994 |
| WO | PCT/US95/03785 | 3/1995 |
| WO | PCT/US95/02593 | 9/1995 |
| WO | PCT/US94/11635 | 1/1996 |
| WO | PCT/US94/11748 | 1/1996 |
| WO | PCT/US95/07960 | 1/1996 |
| WO | PCT/US95/07961 | 1/1996 |
| WO | PCT/US96/05978 | 11/1996 |
| WO | PCT/US96/09598 | 12/1996 |
| WO | 02/32333 | 4/2002 |

OTHER PUBLICATIONS

Graham, Ron; What Is a PID Controller?; 1995, The Engineer's Companion (see attached).*

Beadling, Lee "Electrosurgery: Sculpting the future of arthroscopy," Orthopedics Today.

(Continued)

Primary Examiner—Roy D. Gibson
(74) Attorney, Agent, or Firm—Fish & Richardson P.C.

(57) ABSTRACT

A thermal energy controller system useful in medical procedures includes a controller coupled to a probe, and a thermal element to vary probe temperature. The controller includes memory storing a non-continuous algorithm that permits user-selectable settings for various probe types such that controller operation is self-modifying in response to the selected probe setting. Probe output power Pout is constant in one mode to rapidly enable probe temperature to come within a threshold of a target temperature. The controller can then vary Pout dynamically using a proportional-integral-derivative (PID) algorithm Pout=Kp·P+Ki·I+Kd·D, where feedback loop coefficients Kp, Ki, Kd can vary dynamically depending upon magnitude of an error function e(t) representing the difference between a user-set desired target temperature and sensed probe temperature. Advantageously, target temperature can be rapidly attained without overshoot, allowing the probe system to be especially effective in arthroscopic tissue treatment.

82 Claims, 11 Drawing Sheets

U.S. PATENT DOCUMENTS

| | | |
|---|---|---|
| 1,908,583 A | 5/1933 | Wappler |
| 1,916,722 A | 7/1933 | Ende |
| 1,932,258 A | 10/1933 | Wappler |
| 1,943,543 A | 1/1934 | McFadden |
| 1,983,669 A | 12/1934 | Kimble |
| 2,002,594 A | 5/1935 | Wappler et al. |
| 2,004,559 A | 6/1935 | Wappler et al. |
| 2,056,377 A | 10/1936 | Wappler |
| 2,224,464 A | 12/1940 | Wolf |
| 2,275,167 A | 3/1942 | Bierman |
| 2,888,928 A | 6/1959 | Seiger |
| 3,152,590 A | 10/1964 | Zurdo et al. |
| 3,163,165 A | 12/1964 | Isikawa |
| 3,460,539 A | 8/1969 | Anhalt, Sr. |
| 3,595,239 A | 7/1971 | Petersen |
| 3,768,482 A | 10/1973 | Shaw |
| 3,828,780 A | 8/1974 | Morrison, Jr. |
| 3,870,047 A | 3/1975 | Gonser |
| 3,901,242 A | 8/1975 | Storz |
| 3,902,494 A | 9/1975 | Haberlen et al. |
| 3,920,021 A | 11/1975 | Hiltebrandt |
| 3,920,022 A | 11/1975 | Pastor |
| 3,938,527 A | 2/1976 | Rioux et al. |
| 3,987,795 A | 10/1976 | Morrison |
| 4,189,685 A | 2/1980 | Doss |
| 4,196,734 A | 4/1980 | Harris |
| 4,218,733 A * | 8/1980 | Maselli ..................... 700/37 |
| 4,315,510 A | 2/1982 | Kihn |
| 4,346,715 A | 8/1982 | Gammell |
| 4,350,168 A | 9/1982 | Chable et al. |
| 4,411,266 A | 10/1983 | Cosman |
| 4,448,198 A | 5/1984 | Turner |
| 4,531,524 A | 7/1985 | Mioduski |
| 4,565,200 A | 1/1986 | Cosman |
| 4,597,379 A | 7/1986 | Kihen et al. |
| 4,644,955 A | 2/1987 | Mioduski |
| 4,672,962 A | 6/1987 | Hershenson |
| 4,712,559 A | 12/1987 | Turner |
| 4,800,899 A | 1/1989 | Elliott |
| 4,846,196 A | 7/1989 | Wiksell et al. |
| 4,907,589 A | 3/1990 | Cosman |
| 4,920,978 A | 5/1990 | Colvin |
| 4,927,420 A | 5/1990 | Newkirk et al. |
| 4,938,761 A | 7/1990 | Ensslin |
| 4,955,377 A | 9/1990 | Lennox et al. |
| 4,966,597 A | 10/1990 | Cosman |
| 4,974,587 A | 12/1990 | Turner et al. |
| 4,979,948 A | 12/1990 | Geddes et al. |
| 5,003,991 A | 4/1991 | Takayama et al. |
| 5,097,844 A | 3/1992 | Turner |
| 5,103,804 A | 4/1992 | Abele et al. |
| 5,106,360 A | 4/1992 | Ishiwara et al. |
| 5,122,137 A | 6/1992 | Lennox |
| 5,151,100 A | 9/1992 | Abele et al. |
| 5,190,540 A | 3/1993 | Lee |
| 5,191,883 A | 3/1993 | Lennox et al. |
| 5,224,492 A | 7/1993 | Takahashi et al. |
| 5,249,585 A | 10/1993 | Turner et al. |
| 5,277,201 A | 1/1994 | Stern |
| 5,277,696 A | 1/1994 | Hagen |
| 5,281,218 A | 1/1994 | Imran |
| 5,304,214 A | 4/1994 | DeFord et al. |
| 5,318,525 A | 6/1994 | West et al. |
| 5,334,193 A | 8/1994 | Nardella |
| 5,342,357 A | 8/1994 | Nardella |
| 5,344,435 A | 9/1994 | Turner et al. |
| 5,348,554 A | 9/1994 | Imran et al. |
| 5,352,868 A | 10/1994 | Denen et al. |
| 5,366,490 A | 11/1994 | Edwards et al. |
| 5,370,645 A | 12/1994 | Klicek et al. |
| 5,370,675 A | 12/1994 | Edwards et al. |
| 5,383,874 A | 1/1995 | Jackson et al. |
| 5,383,917 A | 1/1995 | Desai et al. |
| 5,419,767 A | 5/1995 | Eggers et al. |
| 5,421,819 A | 6/1995 | Edwards et al. |
| 5,423,808 A | 6/1995 | Edwards et al. |
| 5,431,649 A | 7/1995 | Mulier et al. |
| 5,433,708 A | 7/1995 | Nichols et al. |
| 5,433,739 A | 7/1995 | Sluijter et al. |
| 5,433,740 A | 7/1995 | Yamaguchi |
| 5,437,662 A | 8/1995 | Nardella |
| 5,437,664 A | 8/1995 | Cohen et al. |
| 5,443,463 A | 8/1995 | Stern et al. |
| 5,443,470 A | 8/1995 | Stern et al. |
| 5,456,682 A | 10/1995 | Edwards et al. |
| 5,458,596 A | 10/1995 | Lax et al. |
| 5,480,397 A | 1/1996 | Eggers et al. |
| 5,480,398 A | 1/1996 | Eggers et al. |
| 5,484,400 A | 1/1996 | Edwards et al. |
| 5,496,312 A | 3/1996 | Klicek |
| 5,505,730 A | 4/1996 | Edwards |
| 5,514,130 A | 5/1996 | Baker |
| 5,540,681 A | 7/1996 | Strul et al. |
| 5,542,915 A | 8/1996 | Edwards et al. |
| RE35,330 E | 9/1996 | Malone et al. |
| 5,562,720 A | 10/1996 | Stern et al. |
| 5,569,242 A | 10/1996 | Lax et al. |
| 5,573,533 A | 11/1996 | Strul |
| 5,578,008 A | 11/1996 | Hara |
| 5,584,830 A | 12/1996 | Ladd et al. |
| 5,628,771 A | 5/1997 | Mizukawa et al. |
| 5,643,255 A | 7/1997 | Organ |
| 5,688,267 A | 11/1997 | Panescu et al. |
| 5,697,925 A | 12/1997 | Taylor |
| 5,697,927 A | 12/1997 | Imran et al. |
| 5,743,903 A | 4/1998 | Stern et al. |
| 5,786,705 A | 7/1998 | Bui et al. |
| 5,843,075 A | 12/1998 | Taylor |
| 5,871,481 A | 2/1999 | Kannenberg et al. |
| 5,931,835 A | 9/1999 | Mackey |
| 5,954,719 A | 9/1999 | Chen et al. |
| 6,074,386 A | 6/2000 | Goble et al. |
| 6,086,581 A | 7/2000 | Reynolds et al. |
| 6,099,524 A | 8/2000 | Lipson et al. |
| 6,135,999 A | 10/2000 | Fanton et al. |
| 6,162,217 A | 12/2000 | Kannenberg et al. |
| 6,409,722 B1 * | 6/2002 | Hoey et al. ................... 606/34 |
| 6,488,679 B1 * | 12/2002 | Swanson et al. .............. 606/40 |
| 2001/0029369 A1 | 10/2001 | Kannenberg et al. |

OTHER PUBLICATIONS

Bradley, James et al "Monopolar ElectroThermal Capsulorrhapyh," *Applications in Electrothermal Arthroscopy,* Case Report No. S2.

Davis, Robert "New shoulder surgery puts Shark back in the swing," *USA Today,* A11–A12, 1998.

Fanton, Gary S. "Monopolar Electrothermal Arthroscopy For Treatment of Shoulder Instability in the Athlete," *Operative Techniques in Sports Medicine,* vol. 8, No 3 (Jul.), pp. 242–249, 2000.

Lopez, Mandi J. et al. "The Effect of Radiofrequency Energy on the Ultrastructure of Joint Capsular Collagen," *Arthroscopy: The Journal of Arthroscopic and Related Surgery,* vol. 14, No 5 (Jul.–Aug.), pp. 495–501, 1998.

Philippon, Marc J. "Arthroscopic Partial Labrectomy and Thermal Synovectomy Utilizing Monpolar RF Energy Case Report," *Applications in Electrothermal Arthroscopy,* Case Report No. H1.

Sluyter, Menno E. "Radiofrequency Lesions in the Treatment of Cervial Pain Syndromes," *Radionics,* pp. 1–24, 1990.

"Tissue Temperature Control ElectroThermal Arthroscopy Probe," *TAC–C II,* 2000.

*Temperature Matters,* 1998.

* cited by examiner

| Ramp 1 | Kp1, Ki1, Kd1 | Final Target Temp 1 | /176 |
|--------|---------------|---------------------|------|
| ⋮ | ⋮ | ⋮ | |
| Ramp N | Kpn, Kin, Kdn | Final Target Temp n | /178 |

PID_Control procedure

METHOD AND APPARATUS FOR CONTROLLING A TEMPERATURE-CONTROLLED PROBE

RELATIONSHIP TO PENDING APPLICATION

This is a continuation-in-part of applicant's U.S. patent application Ser. No. 09/738,944 filed 14, Dec. 2000 now abandoned and entitled "Method and Apparatus for Controlling a Temperature-Controlled Probe", which application is a continuation of U.S. patent application Ser. No. 09/296,690 filed 21, Apr. 1999, now U.S. Pat. No. 6,162,217 (issued 19, Dec. 1999), entitled "Method and Apparatus for Controlling a Temperature-Controller Probe".

FIELD OF THE INVENTION

The invention relates generally to medical probe devices, and more particularly to probes whose temperature may be controlled in a thermally-discontinuous environment to vary thermal energy delivered to tissue during a medical procedure.

BACKGROUND OF THE INVENTION

The most abundant tissue in the human body is soft tissue, and most soft tissue is collagen. Indeed, over 90% of the organic matter in tendons and ligaments is collagen. The connective tissue in joints is comprised of soft tissue, generally collagen tissue. When soft tissue in a joint is damaged, the healing process is often long and painful.

Well-known methods for addressing the treatment of soft tissue in injured joints include strengthening exercises, open surgery, and arthroscopic techniques. Using current treatments, many people with injured joints suffer from prolonged pain, loss of motion, nerve injury, and some develop osteoarthritis. The soft tissue in many injured joints never heals enough to return the damaged joint to its full range of function.

It is known in the art to apply thermal energy to soft tissue, such as collagen tissue, in joints to try to alter or manipulate the tissue to provide a therapeutic response during thermal therapy. In particular, applying controlled thermal energy to soft tissue in an injured joint can cause the collagenous tissue to shrink, thereby tightening unstable joints.

Medical probes for the rehabilitative thermal treatment of soft tissues are known in the art. Examples of these probes include laser probes and RF heated probes. While these probes meet the basic need for rehabilitative thermal treatment of soft tissues, such as collagen tissues, many suffer from temperature overshoot and undershoot fluctuation, causing unpredictable results in the thermal alteration.

Many existing temperature control methodologies rely upon algorithms that are continuous, for example, algorithms such as disclosed in the above-referenced U.S. Pat. No. 6,162,217 (1999) for a "Method and Apparatus for Controlling a Temperature-Controller Probe". Continuous algorithm-based methods can control temperature well in systems are that themselves continuous, i.e., systems in which there is no abrupt change in media temperature, media consistency, head load, cooling effects, etc.

Other approaches seem to be less successful in their attempts to delivery uniform energy from a probe in a thermally unstable environment. For example U.S. Pat. No. 5,458,596 to Lax, et al., discloses examples of a probe with a proximal and distal end that employs heat for the controlled contraction of soft tissue. But not unlike other prior art probes, probe temperature can become unstable as heat from the probe is dissipated into the mass of the treated tissue. This can be especially troublesome when treating dense tissue, which acts as a heat sink and thereby requires additional energy input to maintain a desired target temperature. The application of additional energy in an attempt to compensate for the heat sink effect can cause an underdamped effect before settling out at the desired temperature.

In general, a system is over-damped when its damping factor is greater than one, and the system will have a slow response time. A system is critically damped when its damping factor is exactly one. A system is under-damped when its damping factor is less than one. In an under-damped system, "ringing" is a problem and can result in the momentary application of temperatures that are too high for the safe heating of soft tissue. When this occurs, damage to the soft tissue may result from charring, ablation or the introduction of unwanted and harmful effects on the soft tissue causing injury.

Typically, medical probes are attached to a controller that controls the probe power output based on an actual temperature measurement from a temperature sensor such as a thermocouple in the probe, and a set predetermined target temperature. The controller is part of a system that includes circuitry to monitor temperature sensed by the temperature sensor. Temperature-controlled probes are designed to provide precise coagulation, to eliminate damage, charring, and bubbles. Different size probes with various configurations are available to treat various joint sizes including the shoulder, knee, ankle, wrist and the elbow.

Precise temperature control of the system in which the probes are used is required during various types of thermal therapy of soft tissue. For example, during hyperthermia, which is defined as the treatment of diseased soft tissue by raising the bodily temperature by physical means, some prior art probes have difficulty in providing smooth and consistent heating because the preferred materials for the energy delivery electrodes are highly thermally responsive materials. Such materials generally do not retain large amounts of heat energy. At initiation, the controller rapidly heats the probe to achieve the target temperature, which can result in an overshoot problem. During application, probe contact with large tissue masses tends to cause underdamped fluctuations in the probe temperature due to vast differences in the temperature of the surrounding tissue mass. Likewise, one skilled in the art will appreciate that similar problems may occur during a desired reduction in the soft tissue temperature.

In addition, different probes have different operating characteristics. Applications using larger probes typically need relatively large amounts of power to reach and maintain the desired temperature. Applications using smaller probes, such as a spine probe, need a well-controlled and precise stable temperature. However, the typical prior art controller uses the same method to control the power output for different probes and does not change the control process in response to different types of probes, further contributing to overshoot and undershoot problems.

Therefore, a method and apparatus are needed that allows the controller to change operation in response to the type of probe attached, preferably while reducing if not eliminating temperature overshoot and oscillation during treatment of tissue with the probe. More preferably, such method and apparatus should more rapidly produce adequate thermal energy at the tissue under treatment without overshooting or otherwise exceeding a desired target temperature, and without prematurely reducing thermal output power. In addition, such probe should be continuously controllable even in a thermally discontinuous environment such as arthroscopic environments.

SUMMARY OF THE INVENTION

The present invention provides a method and system that continuously controls power output to a probe, to maintain a target temperature at tissue treated with the probe by a physician or other medical practitioner. Further, such probe may be successfully used in discontinuous environment such as arthroscopic environments.

The system includes a controller, a probe, and a mechanism that couples the probe to the controller. The probe includes a thermal element that can generate heat or cold, and also includes a temperature sensor that senses temperature at the probe. The system and controller preferably effectively accommodate different probe types by providing at least one selectable probe setting for the probes such that controller operation is modified in response to the selected probe setting. This permits controlling the probe output power to more effectively maintain a desired target temperature, preferably without overshooting or exceeding the target temperature.

The system further includes memory storing at least one set of probe settings, where each stored setting preferably includes at least one gain parameter and corresponds to predetermined operating characteristics for a probe. In practice, a target temperature and a first probe setting that corresponds to a desired set of operating characteristics for a probe is received, and a set of probe settings is selected responsive to the first probe setting. The sensed temperature is compared to the desired target temperature and an error signal is generated. A control function that uses the gain parameter from the selected set of probe settings is applied to the error signal to yield an output control signal. A proportional integral differential (PID) algorithm modifies power delivered to the thermal element in response to the output control signal to attain the desired target temperature.

The presently preferred embodiment goes beyond what was described in U.S. Pat. No. 6,162,217 in more rapidly attaining a desired target temperature without substantial overshoot or otherwise exceeding, the desired target temperature, especially in a discontinuous environment. Although temperature could be well controlled according to U.S. Pat. No. 6,162,217, such control functioned best in a thermally continuous environment, and indeed the described method used a continuous algorithm.

But in certain applications, e.g., an arthroscopic environment, discontinuous probe changes occur because the probe tip is not machine controlled but rather manipulated non-predictably by a medical practitioner. As the probe is moved, as different tissue textures are encountered, discontinuous probe changes occur. Further, arthroscopic pumps that control the flow of saline at room temperature turn-on and turn-off, and contact pressure (or lack thereof) with tissue changes. Thus the present invention employs what may be described as a discontinuous algorithm, in contrast to the continuous algorithm employed in the parent application and in U.S. Pat. No. 6,162,217.

In one mode of operation, the present invention using a discontinuous algorithm that first outputs a constant power Pout until the measured probe temperature is within a desired range of the threshold target probe temperature. At that juncture, the algorithm solves a modified proportional-integration, and derivation(or "PID") algorithm defined as $$Pout = Kp \cdot P + Ki \cdot I + Kd \cdot D$$

where Kp is a proportional gain factor, Ki is an integral gain factor, Kd is a derivative gain factor, and P, I, and D are proportion, integration, and derivative functions. The PID algorithm then maintains, without substantially exceeding, the desired probe temperature with good granularity or resolution.

While in many applications, coefficients Kp, Ki, Kd are constants, these coefficients may be varied dynamically depending upon response of a measured parameter, for example temperature, or perhaps impedance, or perhaps a measured voltage magnitude.

Thus, the present invention enables probe temperature to rapidly be ramped in magnitude to a set-point value close to the desired target probe temperature, and thereafter to be controlled with the PID algorithm with much finer granularity of control. As a result, overshoot is minimized.

Other features and advantages of the invention will appear from the following description in which the preferred embodiments have been set forth in detail, in conjunction with their accompanying drawings.

DETAILED DESCRIPTION OF THE PREFERRED EMBODIMENTS

Figure 14:
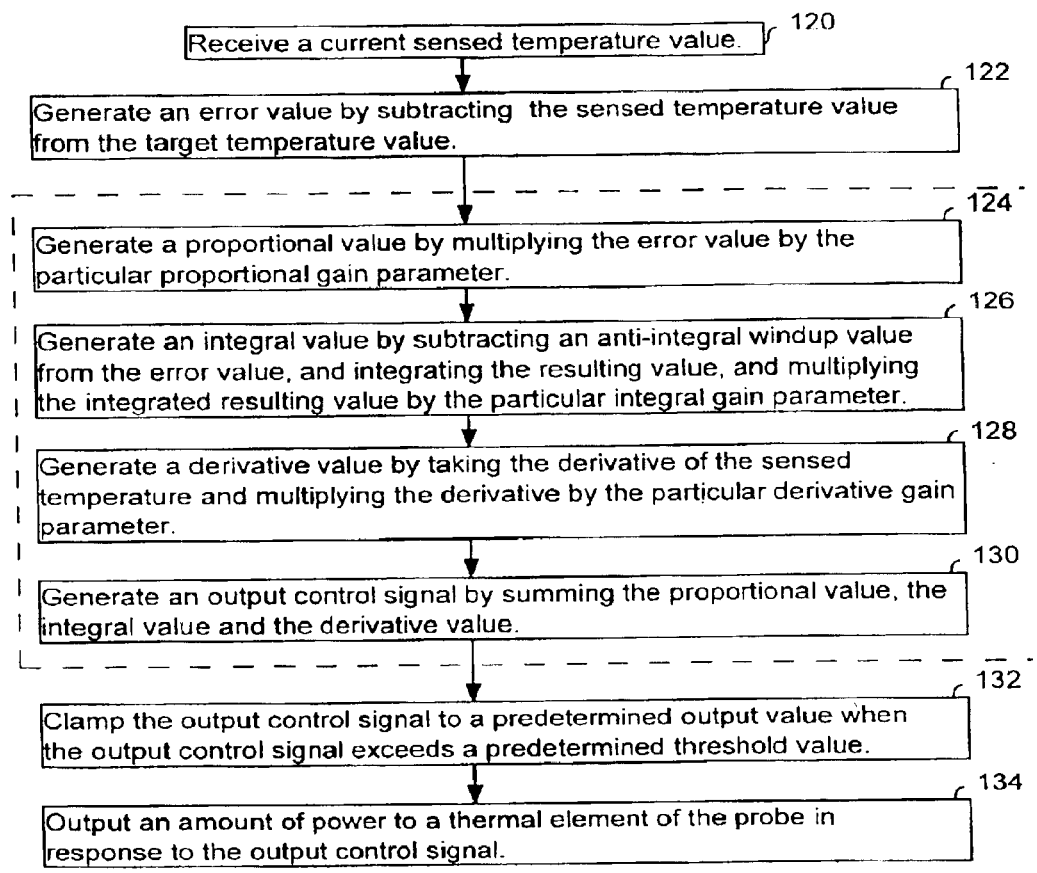
FIG. 14 is a detailed flowchart of step 188 of FIG. 13.
Figure 15:
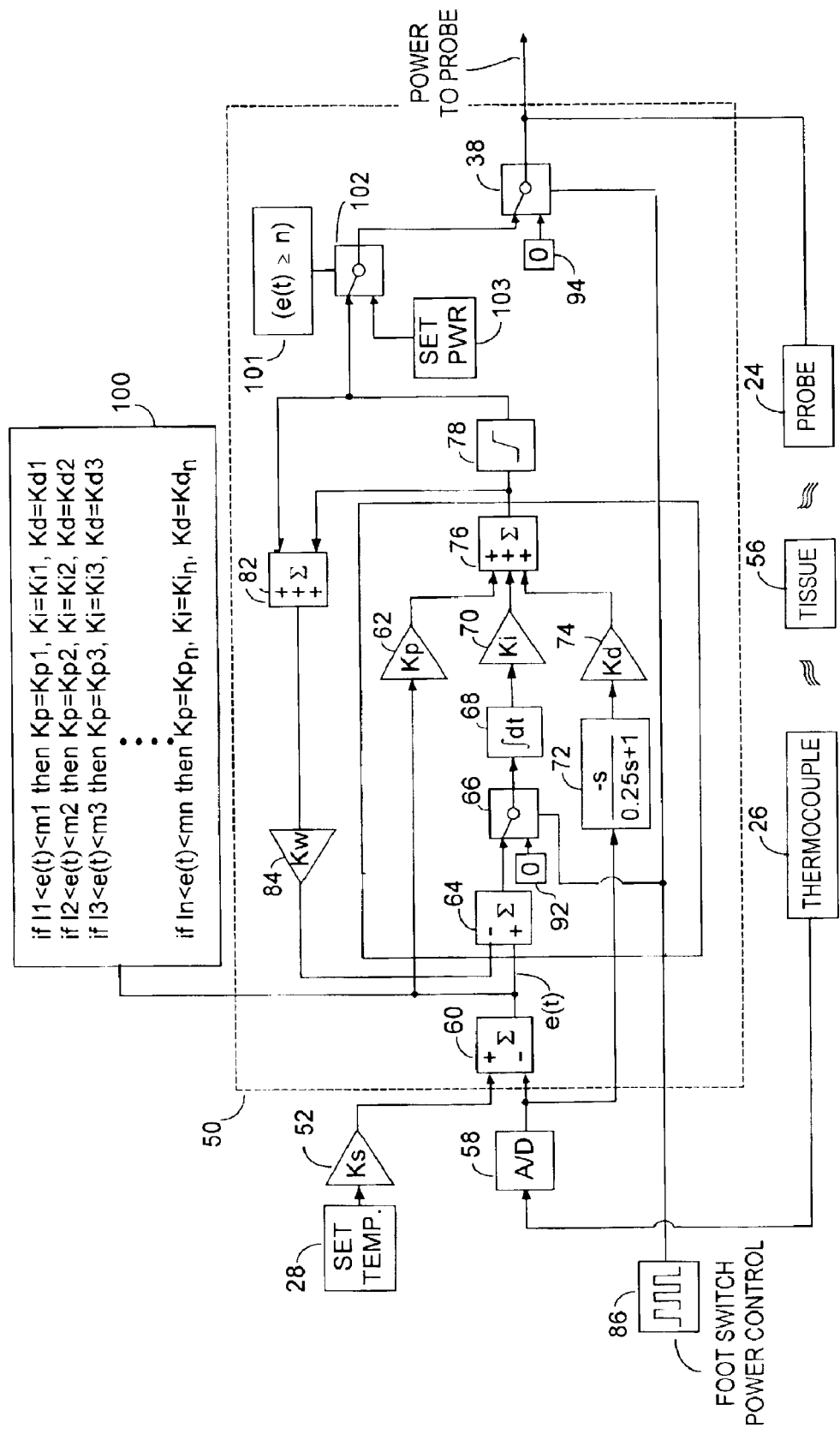
FIG. 15 illustrates an additional and presently preferred embodiment of a discontinuous proportional-integral-derivative (PID) control function, according to the present invention.

The presently preferred embodiment of the present invention is depicted in FIG. 15. However to arrive at a better understanding of FIG. 15, it is useful to first consider FIGS. 1–14, which are applicable to the invention described in U.S. Pat. No. 6,162,217 and will lead to a better understanding of the present invention. The inventions described in the '217 patent will be referred to herein as the parent invention, or the invention in the '217 patent.

Figure 1:
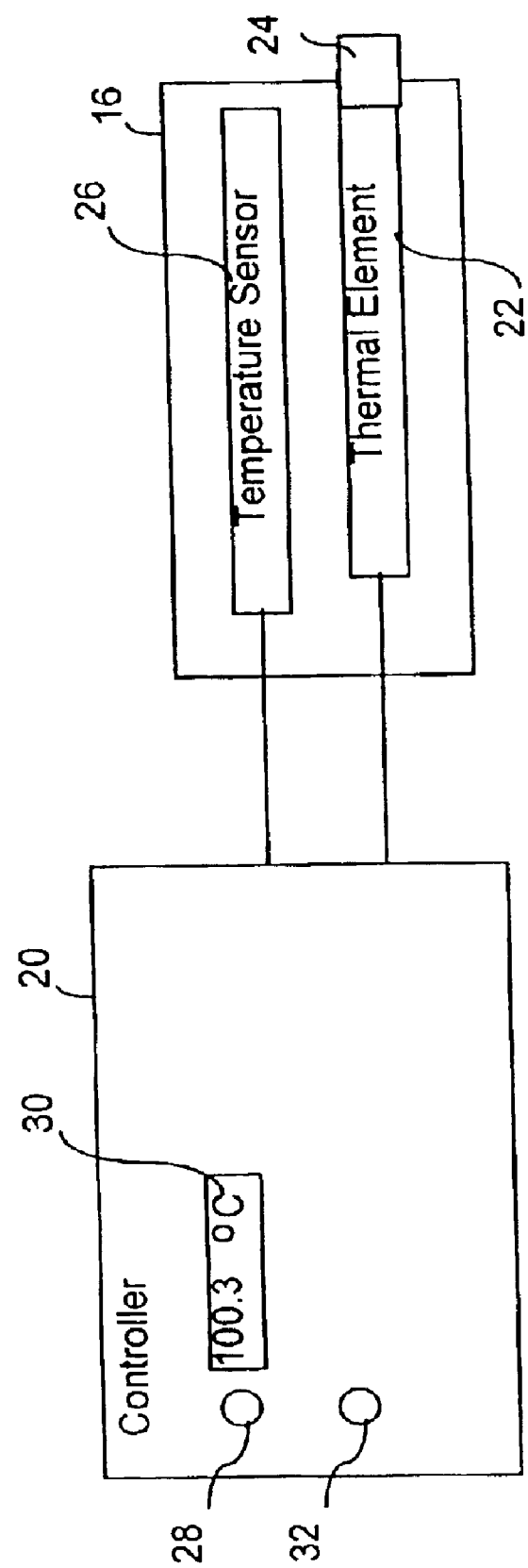
FIG. 1 illustrates a controller and probe, according to an embodiment of the present invention.

Turning, then, to FIG. 1, the presently preferred invention as well as the parent invention include a probe 16 and a temperature controller 20 (or a generator 20) that is coupled to the probe. As shown in FIG. 1, a thermal element 22 is attached to a probe tip 24 of probe 16. Thermal element 22 can be used to alter temperature of tissue being treated with probe 16, by heating or cooling. Without limitation, thermal element 22 may include at least one of a transducer that delivers RF energy to the tissue, a resistive heating element that delivers thermal energy to the tissue, and a cooling element including an element that cools with liquid nitrogen, or electronically, e.g., with a Peltier cell. Exemplary probes and energy delivery systems are described more fully in U.S. Pat. No. 5,458,596 to Lax et al., which is incorporated herein by reference.

Referring to FIG. 1, a temperature sensor 26, such as a thermocouple, senses surrounding temperature. The sensed temperature is coupled to controller 20, which controls the amount of power coupled to thermal element 22, to change temperature of probe tip 24, or to change temperature of the tissue being treated with the probe, e.g., during delivery of RF energy to the tissue.

As was noted, thermal energy can be used to treat soft tissue, and in a preferred embodiment, temperature controller 20 is part of a medical system used by physicians to adjust thermal energy in treating soft tissue. To set a target temperature, a physician (or other medical practitioner) activates a control 28, such as a knob or a digital switch, on the controller 20. The target temperature is displayed on a display 30. Selection of operating characteristics for the controller may be made by the physician, e.g., by adjusting a multiposition switch 32, e.g., a thumbwheel switch, or other switch selection device.

The selection of operating characteristics is determined by the type of probe 16, and the type of tissue subject to thermal therapy using the probe. In other words, each switch position preferably is associated with a probe and tissue combination. The physician may obtain the desired operating characteristics, and therefore switch position, from the manufacturer of the controller 20, for example from the instructions for use (IFU) provided by the controller manufacturer. In this way the physician can set both desired or target temperature and operating characteristics for different probes.

Figures 2, 3:
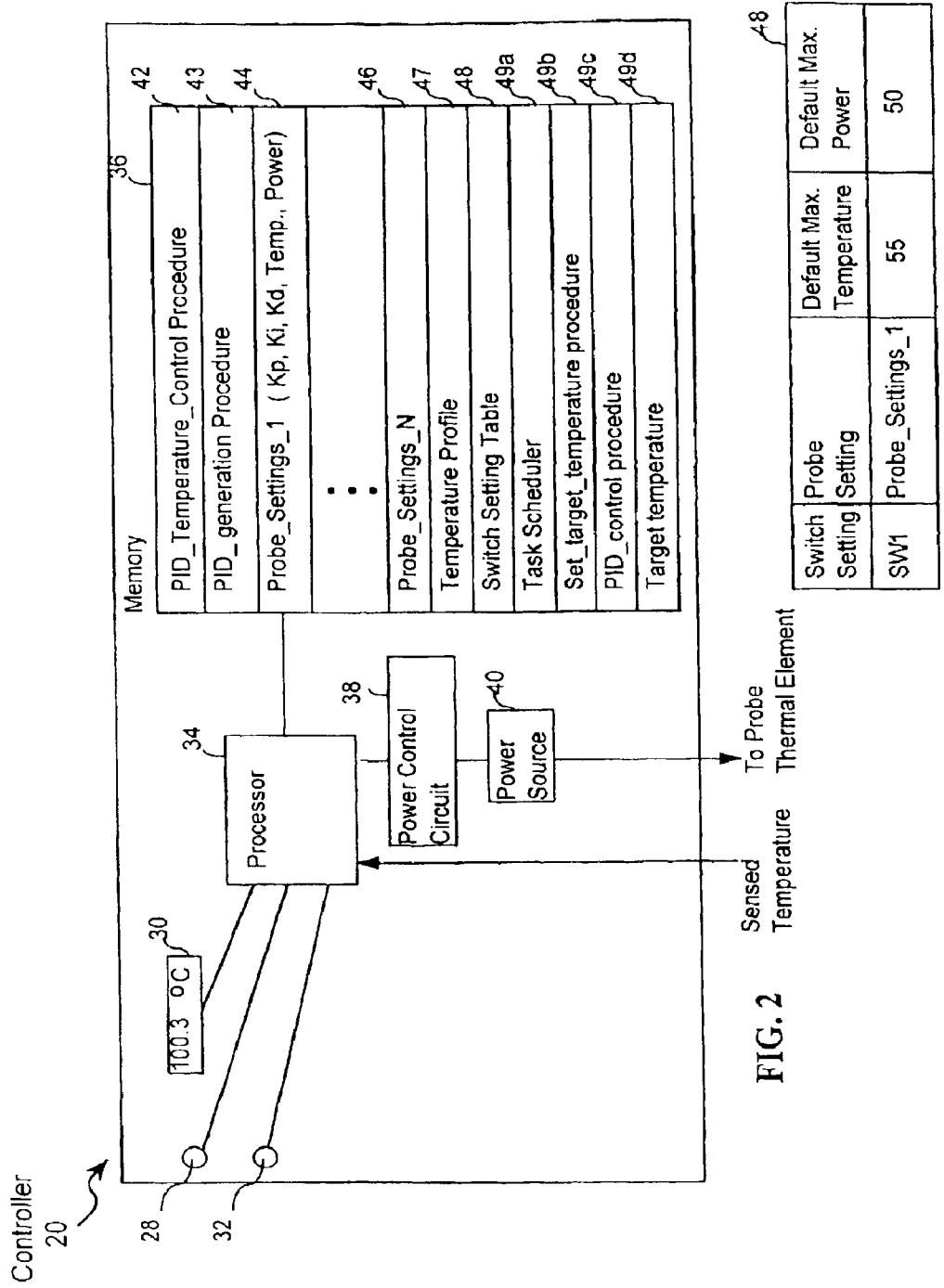
FIG. 2 illustrates the controller of FIG. 1, in accordance with an embodiment of the present invention.
FIG. 3 illustrates an exemplary table, stored in the memory of FIG. 2, associating a particular probe setting with a particular switch position, according to the present invention.

FIG. 2 illustrates controller 20 in more detail. Controller 20 preferably includes a processor 34 that communicates with memory 36, control 28, display 30, switch 32, and a power control circuit 38 that controls a power source 40 that is attached to probe 16. Processor 34 typically includes a microprocessor and peripheral ports that couple to control 28, to display 30, to switch 32, and to power control circuit 38. Memory 36 typically includes semiconductor memory but may instead (or in addition) include other memory types, e.g., magnetic disk memory, and optical storage memory.

The parent invention and the preferred embodiment of the present invention include various forms of a so-called proportional integral differential or PID. As shown in FIG. 2, memory 36 stores a PID_Temperature_Control routine or procedure 42, and a PID_generation procedure 43 (described later herein), N sets of probe settings denoted Probe_Settings_1 to Probe_Settings_N, 44 to 46, respectively, a Temperature Profile 47, and a Switch Setting Table 48.

An exemplary probe setting 46 stored in memory 36 includes a proportional gain factor Kp, an integral gain factor Ki and a derivative gain factor Kd, and may further include a default target temperature and a default maximum power value. Processor 34 executes the PID_Temperature_Control procedure 42 to control the probe-temperature using a PID control methodology that is implemented in the PID_generation procedure 43.

Table 1 below shows a preferred set of gain settings.

TABLE 1

GAIN SETTINGS)

| Gain Setting | Proportional Gain Kp | Integral Gain Ki | Derivative Gain Kd |
|---|---|---|---|
| A | 0.031 | 0.008 | 0.008 |
| B | 0.063 | 0.016 | 0.016 |
| C | 0.125 | 0.031 | 0.031 |
| D | 0.250 | 0.125 | 0.063 |
| E | 0.500 | 0.250 | 0.125 |

Referring to Table 1, higher gain settings such as D and E are beneficial in an application in which the physician must apply heat to a large area of tissue and must move the probe across the tissue. In such application, a greater degree of temperature oscillation may be tolerated due to the larger mass of tissue available to absorb the thermal variations.

Lower gain settings such as A, B and C are beneficial in an application where the probe is stationary for long periods of time and the temperature is varied slowly, e.g., over minutes. The lower gain settings provide more precise temperature control.

In FIG. 2, memory 36 also stores a Task_scheduler 49a, a Set_target_temperature procedure 49b, a PID_control procedure 49c, and a target_temperature 49d (explained later herein with reference to FIGS. 12–14).

In FIG. 3, switch setting table 48 associates each switch 32 setting with a set of probe settings. Table 2, below, depicts exemplary switch settings for table 48, and summarizes the relationship between various switch positions, default temperature, default maximum output power, gain settings, and probe type.

TABLE 2

SWITCH SETTINGS

| Switch Position | Default Temperature (° C.) | Default Maximum Power (W) | Gain Set (see Table 1) | Probe Type |
|---|---|---|---|---|
| 0 | 55 | 50 | C | small |
| 1 | 55 | 40 | C | small |
| 2 | 55 | 30 | C | small |
| 3 | 55 | 20 | C | small |
| 4 | 67 | 30 | C | large |
| 5 | 67 | 40 | C | large |
| 6 | 67 | 50 | C | large |
| 7 | 60 | 30 | C | large |
| 8 | 60 | 40 | C | large |
| 9 | 60 | 50 | C | large |
| 10 | 55 | 20 | D | small |
| 11 | 55 | 30 | D | small |
| 12 | 67 | 40 | D | large |
| 13 | 67 | 50 | D | large |

TABLE 2-continued

SWITCH SETTINGS

| Switch Position | Default Temperature (° C.) | Default Maximum Power (W) | Gain Set (see Table 1) | Probe Type |
|---|---|---|---|---|
| 14 | 80 | 40 | D | large |
| 15 | 80 | 50 | D | large |

Figure 4:
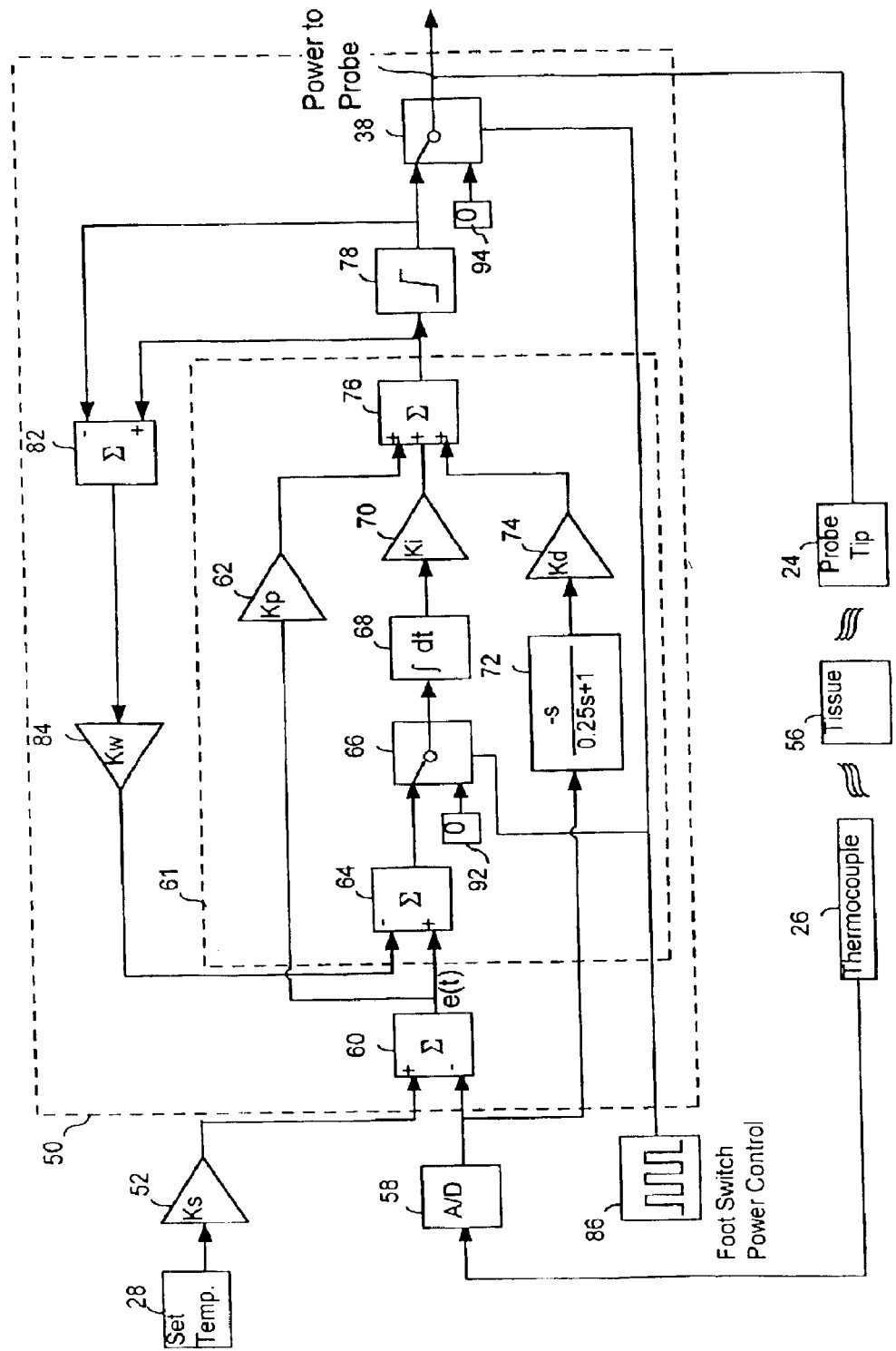
FIG. 4 illustrates a first embodiment of a proportional-integral-derivative (PID) control function, according to the present invention.

Referring now to FIG. 4, a hardware implementation of one embodiment of a proportional-integral-derivative (PID) temperature control is shown, in which block 50 identifies components of a hardware implementation that may be used to carry out a control method according to the present invention. Those skilled in the relevant art of control system design will appreciate that software implementations may be provided to carry out the control method described, based upon the within disclosure. For example, preferably temperature control block 50 is implemented in software in the PID_Temperature_Control procedure 42. However, for ease of illustration, the various embodiments of the present invention will be described with respect to hardware implementation, followed by a description of relevant software and software flowcharts.

As noted, using controller 20, the physician sets the desired temperature using control 28 and associated circuitry, which outputs a digital target temperature signal. As shown in FIG. 4, the digital target temperature signal is multiplied by a constant gain value, Ks, by amplifier 52, where Ks≈10.

During operation, probe tip 24 alters temperature of the tissue 56 under treatment with probe 16. Temperature sensor 26, e.g., a thermocouple, senses surrounding change in temperature and outputs an analog signal that corresponds to the sensed temperature. An analog-to-digital (A/D) converter 58 converts the analog sensed temperature signal to a digital sensed temperature value. The A/D converter 58 may also be calibrated to multiply the sensed temperature signal by a predetermined value, such as ten to match the temperature signal.

A first summer 60 generates an error value or error signal e(t) by subtracting the digital sensed temperature value from the digital target temperature value.

PID generator block 61 generates three signals or values: a proportional value, an integral value, and a derivative value. In a software implementation, PID generator block 61 may be implemented using PID_generation procedure 43 of FIG. 2.

A first amplifier 62 multiplies the error value by the proportional gain factor Kp to generate a proportional signal or value.

Generation of the integral value or signal is as follows. A second summer 64 subtracts an anti-integral windup signal from the error signal e(t), and provides its output via switch 66 an integrator 68. Integrator 68 integrates the adjusted error value, as represented by the 1/s Laplace transform, to generate an intermediate value or signal. In a digital implementation, integrator 68 may use any of several well-known algorithms including without limitation the trapezoidal, Euler, rectangular and Runge-Kutta algorithms. (Digital integrators used in other embodiments to be described herein may similarly be implemented using such algorithms.) A second amplifier 70 multiplies the intermediate value output from integrator 68 by the integral gain factor Ki to generate the integral value.

Derivative unit 72 applies a transfer function to the sensed temperature value to generate an intermediate derivative signal or value to generate the derivative value. A third amplifier 74 multiplies the intermediate derivative signal or value by the derivative gain factor Kd. The transfer function is described later herein, and preferably is represented as a Laplace transform as follows:

$$\frac{-s}{0.25s + 1}$$

A third summer 76 adds the proportional value, the integral value and the derivative value to generate a PID control value or signal.

According to a preferred embodiment of the present invention, the proportional gain factor, the integral gain factor, and the derivative gain factor are determined from the setting of switch 32, the table and the sets of settings in memory 36 before starting the PID control operation. In this way, the PID control function and gains of the proportional, integral and derivative values can be customized to different types of probes.

As shown in FIG. 4, if the PID control value exceeds a predetermined threshold, clamping circuit 78 will output an adjusted PID control value. Thus, clamping circuit 78 outputs a maximum allowed power value to power control circuit 38 to limit or clamp the amount of power supplied to the probe to prevent overheating. If the PID control value does not exceed the predetermined threshold, the clamping circuit 78 outputs the PID control value. In one embodiment, the PID_Temperature_Control procedure determines the default maximum allowed power from the default maximum power value of table 48 of FIG. 3. In an alternate embodiment, the physician manually sets the maximum allowed power.

An antiwindup circuit also helps limit the amount of power. This is accomplished by preventing the integrator from including large power surges, which enables the integrator to more effectively output a stable steady state value and therefore a more stable operating temperature of the probe. A fourth summer 82 subtracts the adjusted PID control value from the PID control value to generate an antiwindup difference. A fourth amplifier 84 multiplies the antiwindup difference by an antiwindup gain factor Kw, typically four, to generate an antiwindup error. The second summer 64 subtracts the antiwindup error from the error value e(t).

Since the adjusted PID control value is typically equal to the PID control value, the antiwindup difference is typically zero and the error value supplied to the integrator 68 is not affected. But when the PID control value is large, for example when power is first turned on, the PID control value may exceed the maximum allowable power, and the PID control value will be clamped. In this case the antiwindup difference will be greater than zero and a positive value will be supplied to the positive input of the second summer 64 to reduce the magnitude of the error value supplied to the integrator, thereby reducing the effect of large surges.

In practice, the physician may control the amount of power supplied to probe 16 use foot switch power control 86 to control position of switches 38 and 66. When foot switch power control 86 is not engaged, a zero value is supplied to the integrator 68 via a first zero block 92 at a first switch position. Similarly, a second zero block 94 is used by the power control circuit 38 such that no power is output to the probe. When the foot switch power control 86 is engaged, switch 66 changes to a second switch position and allows the output of the second summer 64 to flow to the integrator 68. In addition, switch 38 changes to a second switch position and allows the output control value to flow from the clamping circuit 78 to the probe.

Figure 5:
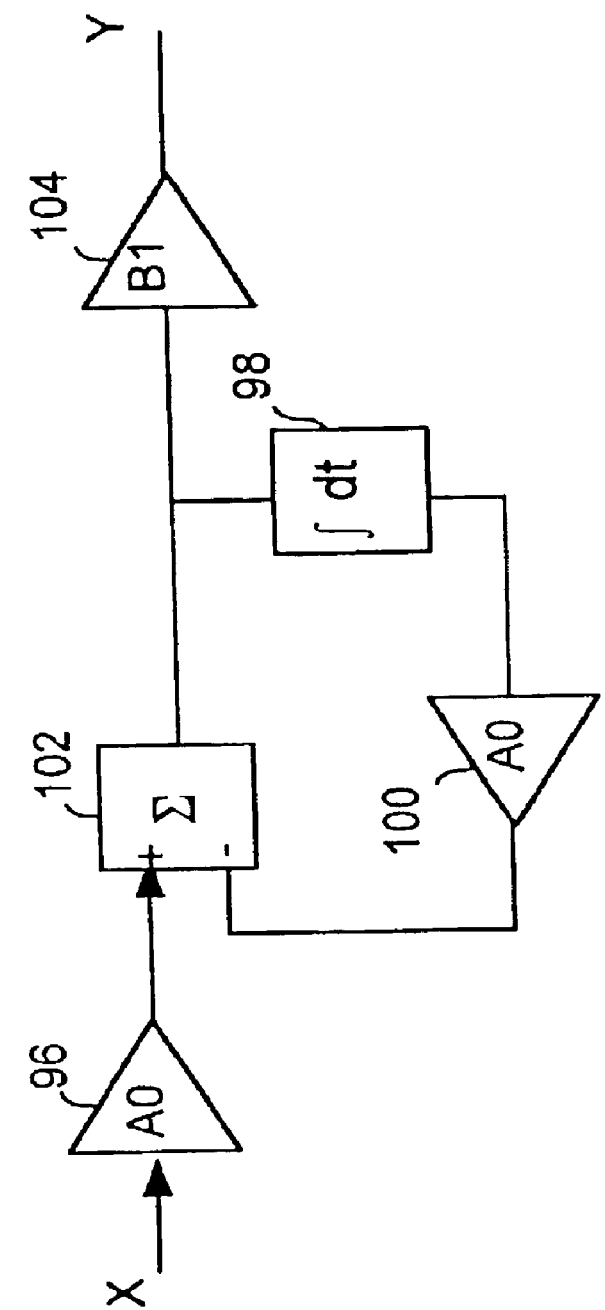
FIG. 5 illustrates an embodiment of the derivative operation of FIG. 4.

The transfer function 72 shown in FIG. 4 may be implemented with the exemplary derivative unit 72 shown in FIG. 5. Transfer function unit 72 receives an input signal X and outputs a value Y. A fifth amplifier 96 multiplies the input signal X by a value A0. Derivative unit 72 includes an integrator 98 that dampens the effect of the derivative function, thereby reducing the sensitivity of the derivative unit 72 to large changes in the input signal, and to noise. As noted, a digital implementation for integrator 98 may be readily implemented using existing algorithms. At power on, integrator 98 output is initialized to zero. A sixth amplifier 100 multiplies the integrator output by A0 to generate a modified integrated signal. A fifth summer 102 subtracts the modified integrated signal from the multiplied input signal, and a seventh amplifier 104 multiplies the summer 102 output by B1 to generate the intermediate integrated value. In a preferred embodiment, A0 is equal to four and B1 is equal to one.

Figure 6:
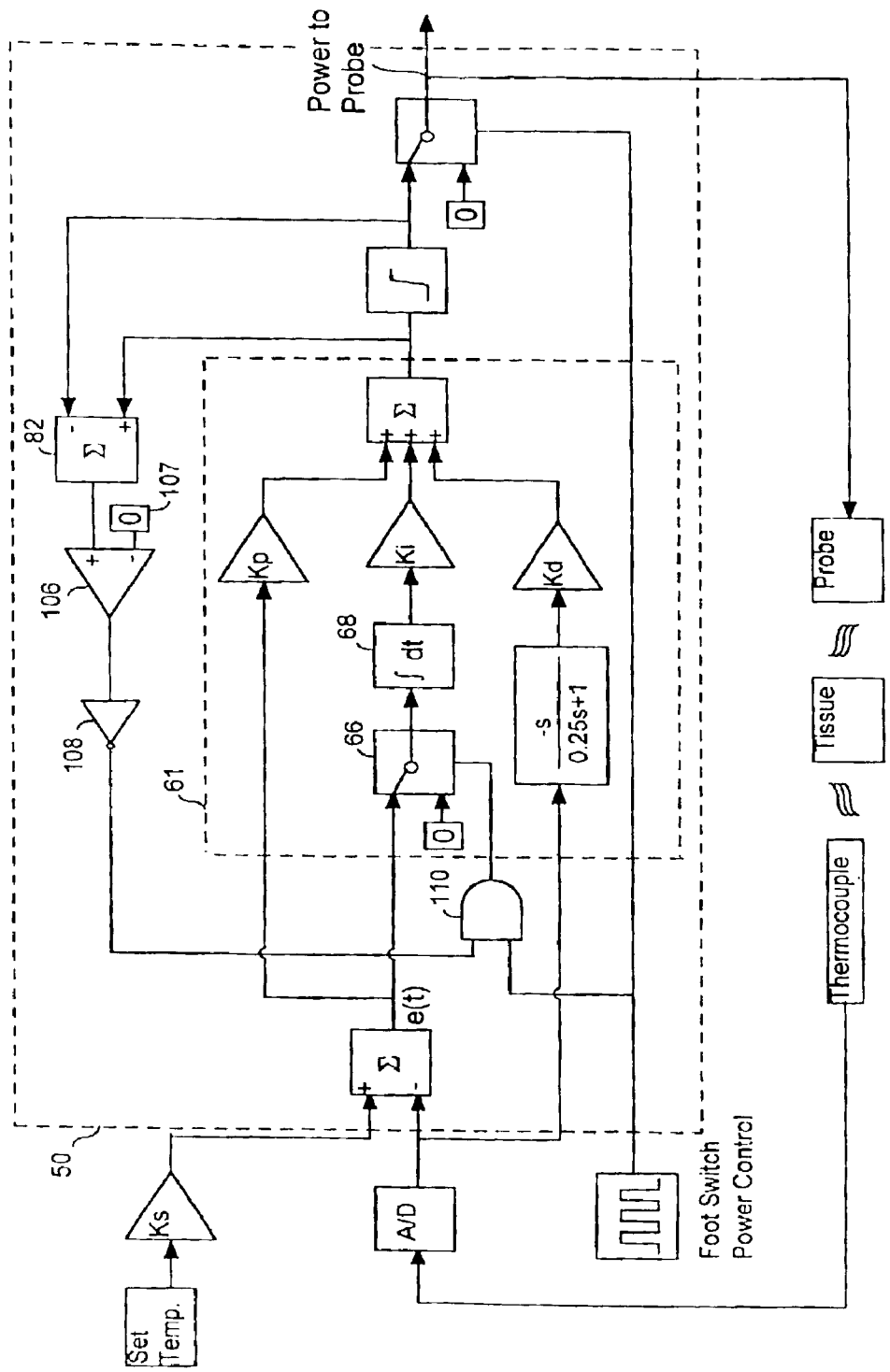
FIG. 6 illustrates a second embodiment of a PID control function, according to the present invention.

The PID control function shown in FIG. 6 is similar to that of FIG. 4 except that the antiwindup function is implemented differently. In FIG. 6, the antiwindup difference is used as a switch to stop further integration, thereby resulting in an improved steady state operation. When the antiwindup difference is equal to zero, integrator 68 can integrate, but when the antiwindup difference is non-zero, integrator 68 stops integrating.

In FIG. 6, fourth summer 82 generates the antiwindup difference, which difference is compared by comparator 106 with a zero value 107. The output from comparator 106 is inverted by inverter 108. In response to inverter 108 and a signal from foot switch control 86, AND gate 110 generates a position control signal that controls switch 64.

More particularly, when the foot switch is not engaged by the physician, the foot switch power control signal has zero value, and the output from AND gate 110 will be a digital zero value, and switch 64 moves to the first switch position to output a zero value, thereby preventing the integrator 68 from integrating.

However, when the foot switch is engaged, the foot switch power control signal is a digital one value, and the AND gate 110 will respond to the antiwindup circuit. When the antiwindup difference is equal to zero, comparator 106 outputs a digital zero value that is inverted to a digital one by inverter 108. Since the inverter 108 now outputs a digital one value, the AND gate 110 outputs a digital one value, and switch 64 is positioned at the second switch position, as shown in FIG. 6, and the integrator 68 integrates the error signal e(t).

When the antiwindup difference is not equal to zero, the antiwindup difference has a positive value, comparator 106 outputs a digital one value and inverter 108 outputs a zero value. In response to the zero value from inverter 108, the AND gate 110 outputs a digital zero value and switch 64 is positioned at the first switch position to output the zero value to the integrator 68, thereby preventing the integrator 68 from integrating.

Figure 7:
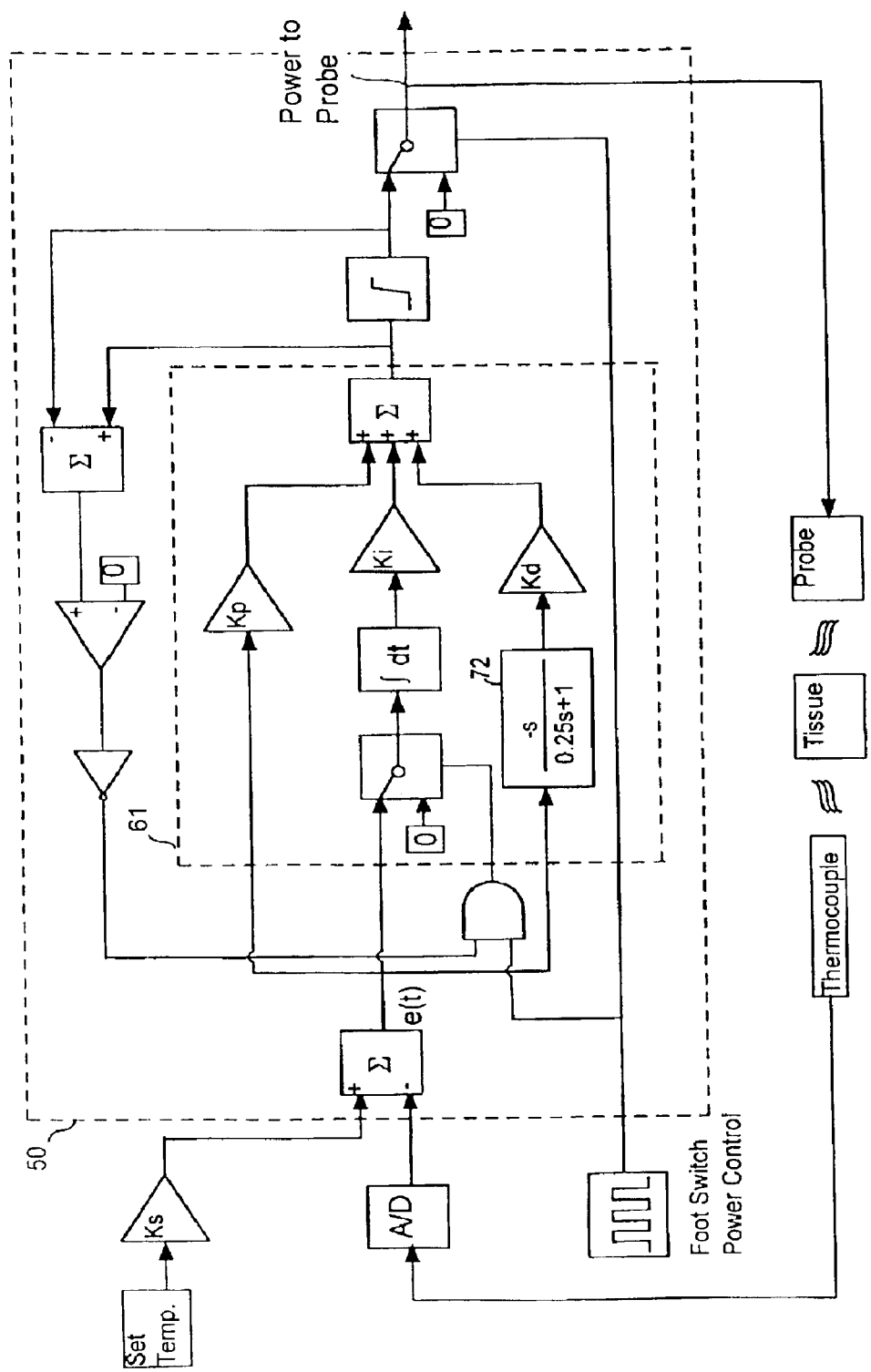
FIG. 7 illustrates a third embodiment of a PID control function, according to the present invention.

The PID control function shown in FIG. 7 is similar to that shown in FIG. 6 except that the error signal e(t) is supplied to the derivative block 72.

Figure 8:
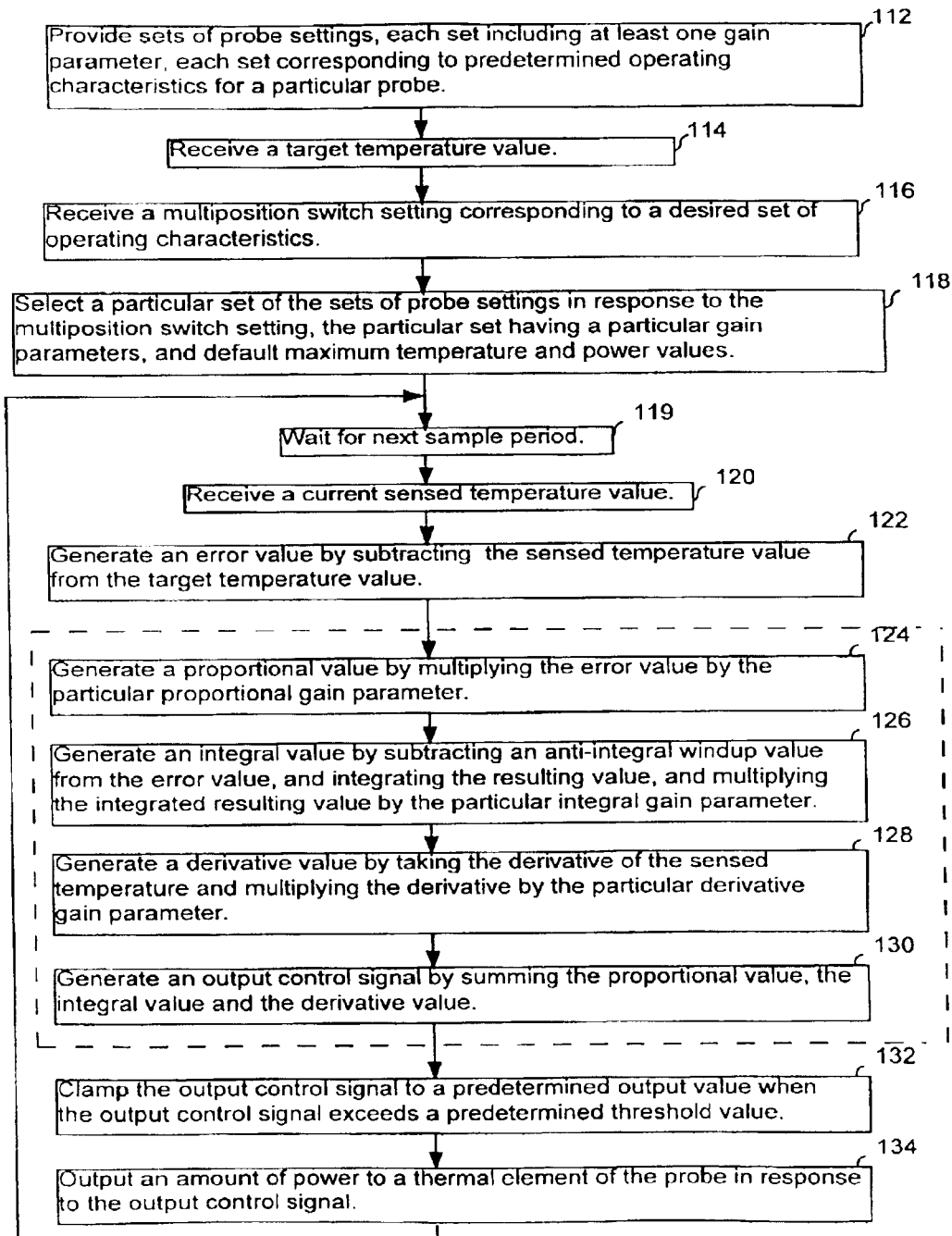
FIG. 8 is a flowchart of the PID control function of FIG. 4.

FIG. 8 is a flowchart of the PID_Temperature_Control procedure 42 of FIG. 2, used to implement the PID control method of FIG. 4. In step 112, sets of probe settings and a table associating the probe settings with switch settings are provided in the memory, as described above. Each set corresponds to predetermined operating characteristics for a particular probe. In step 114, the PID_Temperature_Control procedure 42, receives a target temperature. The target temperature can be set by the physician, for example in conjunction with display 30. The target temperature value used by the PID temperature controller is the temperature set by the physician, for example in degrees Celsius, multiplied by a factor, such as ten. In step 16, the PID_Temperature_Control procedure 42 receives a first setting corresponding to a desired set of operating characteristics from the multiposition switch.

In step 118, the PID_Temperature_Control procedure 42 selects a particular set of the sets of probe settings in response to the multiposition switch setting. The particular set has the proportional, integral and derivative gain factors, Kp, Ki and Kd, respectively, as described above, that will be used by the PID_generation procedure. If the physician has not set a target temperature, the default target temperature stored in memory for the selected switch setting is used. In step 119, the PID_Temperature_Control procedure waits a predetermined amount of time before the next sample period. In one embodiment the predetermined amount of time is equal to 20 ms. In other words, the PID_Temperature_Control procedure samples the sensed temperature value output by the probe every 20 ms. In one implementation, the PID_Temperature_Control procedure uses interrupts to trigger the sample periods.

In step 120, a sensed temperature value is received. Similar to the target temperature, the sensed temperature value represents the actual temperature in degrees Celsius and multiplied by a factor of ten. In step 122, an error value is generated by subtracting the sensed temperature from the target temperature.

As shown by the dashed lines, steps 124 to 130 are implemented in the PID_generation procedure 43 of FIG. 2, which is invoked by the PID_Temperature_Control procedure. The PID_generation procedure also corresponds to the PID generation block 61 shown in FIG. 4. In step 124, a proportional value is generated by multiplying the error value by the particular proportional gain parameter, Kp. In step 126, an integral value is generated by subtracting the anti-integral windup value from the error value, integrating the resulting value of the subtraction and multiplying the integrated adjusted error value by the particular integral gain parameter, Ki.

Integrator 68 can be implemented using various well known algorithms. In step 128, a derivative value is generated by applying a derivative transfer function to the sensed temperature value, as described above, and multiplying the result of the transfer function by the particular derivative gain parameter. In step 130, an output control signal is generated by summing the proportional value, the integral value and the derivative value.

In step 132, the output control signal is clamped to a predetermined output value when the output control signal exceeds a predetermined threshold value. The predetermined threshold value is the default set power from Table 2, or the predetermined threshold value can be manually set by the physician. Alternately, based on the multiposition switch setting, the default maximum power value stored in one of the tables, described above, is used. In step 134, an amount of power is output to the thermal element of the probe in response to the output control signal, and the process repeats at step 120.

Figure 9:
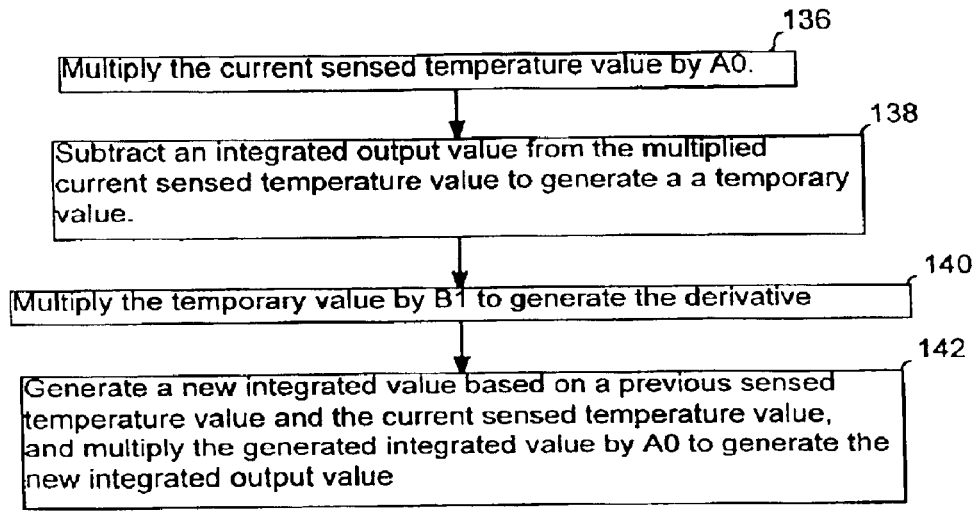
FIG. 9 is a flowchart of the derivative operation of FIG. 5 that is used in step 128 of FIG. 8.

FIG. 9 is a detailed flowchart of step 128 shown in FIG. 8, which step generates the derivative value. In step 136, the current sensed temperature value is multiplied by a first constant, A0. At step 138, a temporary value is generated by subtracting an integrated output value from the multiplied current sensed temperature. Initially, the integrated output value is zero and is modified with each current sensed temperature reading. In step 140, the temporary value is multiplied by a second constant, B1, to generate the derivative value. In step 142, a new integrated value is generated based on a previous sensed temperature value and the current sensed temperature value. Again, the integration may be carried out using any of several well known algorithms. The new integrated value is multiplied by the first constant, A0, to generate another integrated output value which is used in subsequent calculations. As described above, preferably, the first constant, A0, is equal to four and the second constant, B1, is equal to one.

FIGS. 8 and 9 depict an alternate embodiment in which error values are input to the derivative operation instead of the sensed temperature values.

Figure 10:
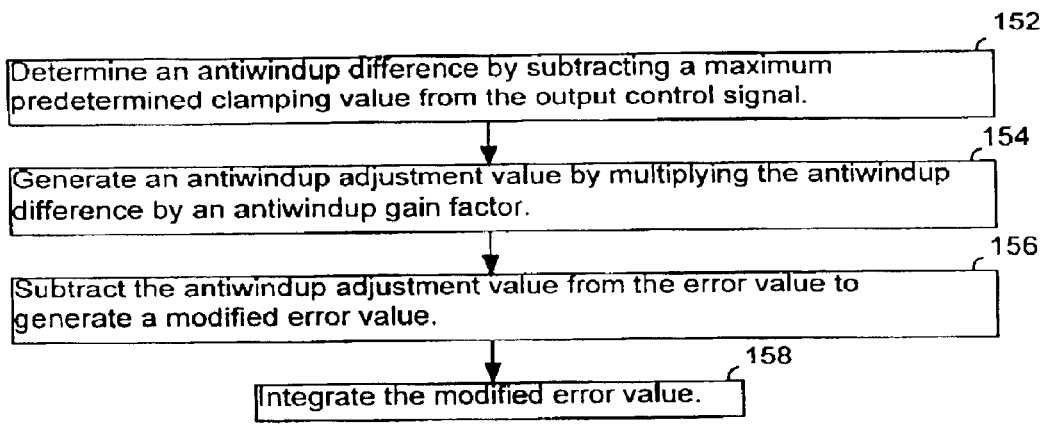
FIG. 10 is a flowchart of a first embodiment of an antiwindup function, according to the present invention.

FIG. 10 is a flowchart of PID_Temperature_Control procedure 42 shown in FIG. 4, and used to implement the antiwindup function of FIG. 4. In step 152, an antiwindup difference is determined by subtracting a maximum predetermined clamping value from the output control signal. In step 154, an antiwindup adjustment value is generated by multiplying the antiwindup difference by an antiwindup gain factor. In step 156, the antiwindup adjustment value is subtracted from the error value to generate a modified error value, which modified error value is integrated at step 158.

Figure 11:
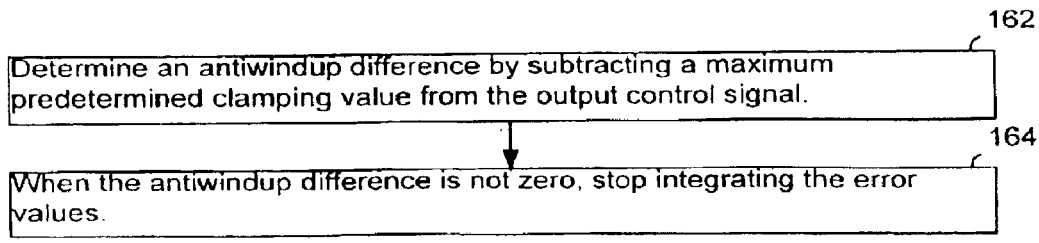
FIG. 11 is a flowchart of a second embodiment of an antiwindup function, according to the present invention.

FIG. 11 is a flowchart of the PID_Temperature_Control procedure 42 of FIG. 2, used to implement the alternate embodiment of the antiwindup function of FIG. 6. In step 162, an antiwindup difference is determined by subtracting a maximum predetermined clamping value from the output control signal. In step 164, when the antiwindup difference is not zero, the procedure stops integrating the error values.

Figures 12, 13:
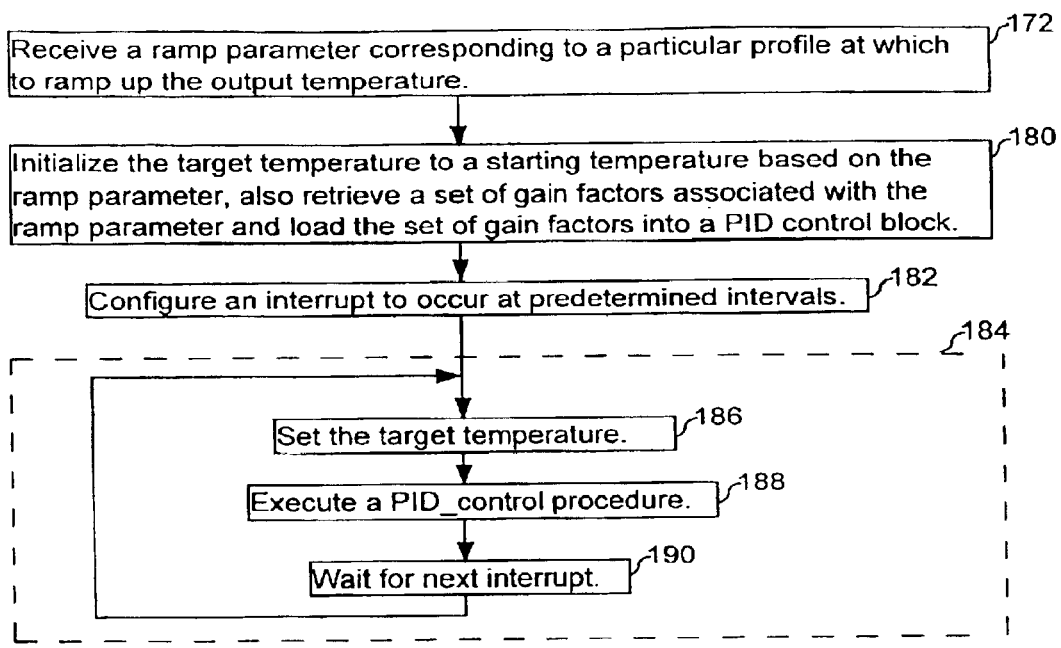
FIG. 12 is a flowchart of an embodiment that varies target temperature to attain final target temperature, according to the present invention.
FIG. 13 is an exemplary temperature profile stored in the memory of FIG. 2.

FIG. 12 is a flowchart of the PID_Temperature_Control procedure 43 of FIG. 2, used to implement the variable temperature setting. Physicians may want to change the temperature profile depending on the application. When operating on large body joints, the physician may want to use the probe in a high power mode to heat the probe quickly and maintain the target temperature. However, when operating on the spine, the physician may want to use a low power mode with a very controlled temperature and no overshoot.

In this embodiment of the invention, the physician via the multiposition switch can select a particular temperature profile (see block 47, FIG. 2). The physician also may set a final target temperature. In FIG. 12, in step 172, in the PID_Temperature_Control procedure, the selected switch position corresponds to a particular temperature profile with a ramp parameter at which to ramp up the output temperature. Referring also to FIG. 13, additional exemplary temperature profiles are shown. Each profile 176, 178 stores a ramp parameter (Ramp 1, Ramp N), gain settings, and a final target temperature. Referring back to FIG. 12, in step 180, in response to the switch position, the target temperature is initialized to a starting temperature based on the ramp parameter. The set of gain factors associated with the ramp parameter are retrieved and loaded into a PID control block for use by the PID_control procedure. In step 182, the PID_Temperature_Control procedure configures the microprocessor to generate an interrupt at predetermined intervals, preferably every 20 ms.

The steps in block 184 are executed in response to the interrupt. In step 186, the target temperature is set using the Set_target_temperature procedure (49b, FIG. 2). If step 186 is being executed in response to a first interrupt, the target temperature is already set to the starting temperature. Otherwise, the target temperature is changed by adding the ramp parameter to the target temperature if a predetermined amount of time has elapsed between successive target temperature changes. Preferably, the target temperature is changed every thirty seconds. If the sum of the ramp parameter and the target temperature exceeds the final target temperature, then the target temperature is set to the final target temperature.

In step 188, the PID_control procedure (see element 49c, FIG. 2) is executed to control the temperature of the probe. The PID_control procedure is executed at each interrupt, every 20 ms. The PID_control procedure will be shown in further detail in FIG. 14. In step 190, the PID_Temperature_Control procedure waits for the next interrupt to occur.

Preferably, the microprocessor executes a task scheduler (49a, FIG. 2), such as a round-robin task scheduler, to generate the interrupts and to execute the Set_target_temperature procedure and the PID_control procedure as tasks. The target temperature is stored in the memory (see element 49d, FIG. 2) for access by both the Set_target_temperature procedure and the PID_control procedure.

In an alternate embodiment, the Set_target_temperature procedure changes the gain factors in addition to changing the target temperature. For example, for a particular switch position setting, a low power application with a very controlled temperature is desired. Based on the switch position, the PID_Temperature_Control procedure sets an initial target temperature that is much lower than the final target temperature. The PID_Temperature Control procedure also uses the predetermined set of gain values associated with the particular switch position setting and the interrupts are configured. In response to the interrupts, the Set_target_temperature procedure and the PID_control procedure are executed every 20 ms.

After thirty seconds have passed, the Set_target_temperature procedure increments the initial target temperature by a predetermined amount, such as one degree, to generate the next target temperature. In this way, the Set_target_temperature procedure increments the intermediate target temperature until the final desired target temperature is reached. As a result, the temperature of the probe is very well-controlled and overshoot is substantially avoided.

In FIG. 14, a flowchart of the PID_Control procedure of step 188 of FIG. 12 is shown. The PID_Control procedure uses steps 120–134 of FIG. 8, which were described above. The antiwindup adjustment of FIG. 10 or 11 can be used with the PID_Control procedure of FIG. 14.

Note that depending on the type of probe, the target temperature can be set to increase or decrease the tissue temperature. Therefore, the method and apparatus can control both high temperature and low temperature probes to heat or cool tissue.

Turning now to FIG. 15, a presently preferred embodiment of a PID control procedure is depicted. Unless otherwise noted, elements or blocks in FIG. 15 bearing like reference numerals to elements previously described may be considered identical to the previously described elements. Note the addition of two new blocks, namely blocks 100–103.

A design goal of the presently preferred embodiment is that the actual probe temperature should rapidly approach a desired threshold target probe temperature and thereafter be very precisely controlled such that there is not substantial temperature overshoot, preferably not even for short signal time intervals. Accordingly, in the embodiment of FIG. 15, several facets of discontinuous control algorithms are used to control the difference between actual measured temperature and the desired target temperature. The use of dynamically selectable discontinuous algorithms permits optimizing probe power output for a specific time period during the treatment cycle.

Initially, a probe according to the presently preferred embodiment will be operated at a constant power out (Pout) mode, during which probe temperature can rapidly ramp up towards a desired threshold target temperature. Once within a threshold range of this target temperature, discontinuous regions of a control PID algorithm as shown in FIG. 15, block 100, can more finely control probe temperature. The end result is that the desired probe temperature is rapidly reached and maintained, even in arthroscopic environments.

This new approach differs from the continuous PID control algorithms described in the '217 patent in that discontinuities exist in the present algorithm, as shown by block 100 in FIG. 15. The continuous algorithms in the '217 patent were fairly predictive but tended to be conservative in that the control mechanism tended to reduce the power delivered to the probe before reaching the target temperature. By contrast, the PID control algorithm shown in block 100, FIG. 15 tends to more rapidly attain the target temperature using a faster ramping up procedure, and provides relatively fine granularity of optimum rate parameters for power control.

The presently preferred embodiment seeks to attain without overshooting or otherwise exceeding the desired target temperature by executing a modified PID algorithm definable as:

$$Pout = Kp \cdot P + Ki \cdot I + Kd \cdot D$$

where Pout is output power, Kp is a proportional gain factor, Ki is an integral gain factor, Kd is a derivative gain factor, and P, I, and D are proportion, integration, and derivation functions. In conjunction with the feedback loop shown in FIG. 15, the modified PID algorithm can adjust the rate at which the probe temperature approaches the target temperature, where the Ki·I factor integrates the temperature difference and tends to increment temperature such that the average temperature becomes the desired target temperature. The result is a more rapid control of probe temperature, without exceeding the target temperature, even as the probe is moved over the tissue under treatment.

In one mode of operation, probe output power is held constant, e.g., Po=k4, where k4 is a desired constant output magnitude. Error signal e(t), which is available as an input to blocks 62, 64, 100 in FIG. 15, provides a measure of how closely the measured parameter is to a target parameter. Although the measured parameter may be impedance, or voltage, or some other variable, in the preferred embodiment, probe temperature is the parameter of interest.

With respect to block 100 in FIG. 15, 11 can represent the measured parameter of interest, e.g., probe tip temperature, and m1 can represent a desired threshold regime. Thus, although the probe is initially operated at Po=k4, a constant, as the probe tip temperature ramps up and becomes sufficiently close to the first threshold regime, the discontinuous PID algorithm will take control of output power Po, e.g., $$Pout = Kp \cdot P + Ki \cdot I + Kd \cdot D$$

Although coefficients Kp, Ki, Kd may be constant in many applications, the present invention permits dynamically altering any or all of these coefficients, depending upon the response of the measured parameter, e.g., probe temperature. Thus, after probe temperature is sufficiently close to a first threshold temperature m1, coefficients in the PID algorithm will be, in the example shown, Kp1, Ki1, Kd1. If probe temperature is close to a second regime, then coefficients can dynamically be changed to Kp2, Ki2, Kd2, and so forth. Again it is understood that ranges of e(t) can be used to select any or all of the appropriate coefficients Kp, Ki, Kd.

The desired result is that after relatively rapidly bringing probe temperature close to (without exceeding) a desired target temperature, the dynamic PID algorithm then causes the probe to deliver thermal power to heat tissue at a desired rate, with an optimal spread of tissue temperature and thermal energy depth, without dramatic changes in tissue surface temperature. Thus, whereas thermal control according to the '217 patent could do a good job in maintaining probe temperature in a thermally stable environment, e.g., surface heating, the discontinuous PID functions used in the present invention can help maintain probe temperature with finely controlled granularity, without substantial overshoot in the greater tissue depths associated with an arthroscopic environment, including treating ligaments.

Thus, FIG. 15, block 100 may be understood to present a set of logic statements to determine the value of Kp, Ki, Kd based upon error signal e(t), according to the presently preferred embodiment. Depending upon the relationship of e(t) compared to predetermined limits $l_n$ and $m_n$, where n is an index, coefficients Kp, Ki, and Kd take on different values. The various limit factors, e.g., $l_1, l_2, \ldots, m_1, m_2, \ldots$ and co-efficient or gain factors $Kp_1, Kp_2, \ldots, Ki_1, Ki_2, \ldots, Kd_1, Kd_2$ preferably will have been stored in memory 36 (see FIG. 3).

At block 101, the Boolean argument e(t)>n controls the state of the power output control circuit, shown herein as 102. The power output control circuit supplies either the PID-calculated amount of power, or the maximum amount of power selected by the physician user at 103.

In summary, initially a probe may be operated at a constant power output level Po=k4 to rapidly bring probe tip temperature close to a desired target temperature. Then using the discontinuous PID algorithm shown in block 100 in FIG. 15, the Kp·P portion of the algorithm looks at the difference between the actual probe temperature (e.g., as determined by sensor 26) and the desired target temperature (e.g., as set by the physician using control 28). The Kd·D portion of the algorithm examines the rate at which the probe temperature is actually approaching the desired target temperature, and the Kd·D portion of the algorithm predicts whether the present settings (and these settings are dynamic) will result in attaining, without exceeding, the target temperature.

It will be appreciated that the above, dynamic, solution avoids tradeoffs inherent in other designs where a system's temperature response could be adjusted to rapidly attain a target temperature, albeit with a relatively large overshoot, or where a system's gain factor could be adjusted for minimal temperature overshoot, albeit with a relatively long time period in which to attain the target temperature.

Further, it will also be appreciated that the above, dynamic, solution better enables the probe to be used in arthroscopic treatments where the probe is continuously being moved across tissue that is at relatively low temperature, e.g., 37° C. The probe movement across relatively cooler tissue presents a thermal load that can make it difficult to elevate the probe temperature to the desired temperature quickly, but without overshoot. This challenge is met by the PID configuration of FIG. 15 in that the algorithm reconfigures the control system dynamically, depending upon whether the probe temperature has just started to move toward the target temperature, or whether the probe temperature is indeed quite close to the target temperature.

Modifications and variations may be made to the disclosed embodiments without departing from the subject and spirit of the invention as defined by the following claims.

What is claimed is:

1. A method of controlling a power output to a probe, the method comprising:
    (a) providing in a memory at least one set of settings for said probe including at least one gain parameter and corresponding predetermined operating characteristics for said probe;
    (b) receiving a target probe temperature;
    (c) receiving a first probe setting corresponding to a desired set of operating characteristics for said probe;
    (d) selecting from said at least one set of probe settings a set of settings in response to said first probe setting;
    (e) generating an error signal e(t) from a comparison of a sensed temperature sensed by a probe temperature sensor and said target probe temperature;
    (f) providing a controller with a control function for generating an output power control signal Pout definable in part by:

$$Pout=k4,$$

when said error signal is greater than or equal to a threshold value, and definable in part by:

$$Pout=Kp \cdot P + Ki \cdot I + Kd \cdot D$$

when said error signal is less than the threshold value;
    where k4 is a constant, Kp is a proportional gain factor associated with said control function, Ki is an integral gain factor associated with said control function, Kd is a derivative gain factor associated with said control function, and P, I, and D are proportion, integration, and derivation functions associated with said control function; and
    (g) using said error signal e(t) to dynamically control at least one of said Kp, Ki, and Kd to determine said Pout; and
    (h) controlling the power output to a probe thermal element responsive to said Pout.

2. The method of claim 1, wherein step (g) includes quantizing said e(t) into one of at least two ranges, and selecting at least two of said Kp, Ki, and Kd as a function of a quantized one of said ranges.

3. The method of claim 1, wherein step (g) includes quantizing said e(t) into one of at least two ranges, and selecting said Kp, Ki, and Kd as a function of a quantized one of said ranges.

4. The method of claim 1, wherein said k4 comprises a maximum power.

5. The method of claim 1, wherein step (f) includes limiting said output control signal to a predetermined output value when said output control signal exceeds a predetermined threshold.

6. The method of claim 1, wherein said integration function I is disabled when said output control signal exceeds a predetermined threshold value.

7. The method of claim 1, wherein said at least one gain parameter further includes a set-specific proportional gain factor and a set-specific integral gain factor.

8. The method of claim 7, wherein providing the controller with the control function further comprises:
    (i) generating said Kp·P by multiplying said error signal e(t) by said selected set-specific proportional gain factor; and
    (ii) generating said Ki·I by integrating said error signal e(t) and multiplying by said selected set-specific integral gain factor.

9. The method of claim 7, wherein:
    said at least one gain parameter further includes a set-specific derivative gain factor, and
    providing the controller with the control function further comprises generating said Kd·D by applying a derivative function to a sensed said temperature to generate an intermediate signal, and multiplying said intermediate signal by said selected set-specific derivative gain factor.

10. The method of claim 1, wherein said at least one gain parameter includes a set-specific proportional gain factor, a set-specific integral gain factor, and a set-specific derivative gain factor.

11. The method of claim 1, further including:
    generating an antiwindup adjustment signal;
    subtracting said antiwindup adjustment signal from said error signal e(t) to yield a modified error signal;
    wherein integration function I integrates said modified error signal.

12. The method of claim 1, further including:
    receiving a ramp parameter corresponding to a particular profile at which to ramp up output power; and
    changing said target temperature responsive to said ramp parameter.

13. A method of controlling a power output to a probe, the method comprising:
    (a) providing in a memory at least one set of settings for said probe including at least one gain parameter and corresponding predetermined operating characteristics for said probe;
    (b) receiving a target probe temperature;
    (c) receiving a first probe setting corresponding to a desired set of operating characteristics for said probe;
    (d) selecting from said at least one set of probe settings a set of settings in response to said first probe setting;
    (e) generating an error signal e(t) from a comparison of a sensed temperature sensed by a probe temperature sensor and said target probe temperature;
    (f) providing a controller with a control function that examines a rate at which said sensed temperature approaches said target temperature, and determines whether said sensed temperature will attain but not exceed said target temperature;
    (g) using said error signal e(t) to dynamically control at least one factor of said control function to determine an output power control signal; and
    (h) controlling the power output to a probe thermal element responsive to said output power control signal.

14. The method of claim 13, wherein using said error signal e(t) comprises quantizing said e(t) into one of at least two ranges, and selecting a characteristic coefficient associated with said closed-loop as a function of a quantized one of said ranges.

15. The method of claim 13, further including replacing said determined output power control signal with a maximum power based on said error signal.

16. The method of claim 13, wherein providing the controller with the control function comprises limiting said output power control signal to a predetermined output value when said output control signal exceeds a predetermined threshold value.

17. A system to control a power output to a probe having a probe thermal element and a probe temperature sensor such that a target probe temperature is maintained at the probe without substantial overshoot, the system comprising:
a controller including a processor and memory, said memory including at least one set of settings for said probe, including at least one gain parameter and corresponding predetermined operating characteristics for said probe, and further including a routine executable by said processor to cause said processor to carry out the following:
(a) to receive said target probe temperature;
(b) to receive a first probe setting corresponding to a desired set of operating characteristics for said probe;
(c) to select from said at least one set of probe settings a set of settings in response to said first probe setting;
(d) to generate an error signal e(t) from a comparison of a sensed temperature sensed by said sensor and said target probe temperature;
(e) to provide said controller with a control function that examines a rate at which temperature approaches said target probe temperature, and determines whether said sensed temperature will attain but not exceed said target temperature;
(f) to use said error signal e(t) to dynamically control at least one factor of said control function to determine an output power control signal; and
(g) to control the power output to said thermal element responsive to said output power control signal.

18. The system of claim 17, wherein said control function is defined in part by:

$$Pout=Kp \cdot P+Ki \cdot I+Kd \cdot D$$

where Pout is said output power control signal, Kp is a proportional gain factor associated with said control function, Ki is an integral gain factor associated with said control function, Kd is a derivative gain factor associated with said control function, and P, I, and D are proportion, integration, and derivation functions associated with said control function.

19. The system of claim 18, wherein said processor quantizes said e(t) into one of at least two ranges, and selects at least two of said Kp, Ki, and Kd as a function of a quantized one of said ranges.

20. The system of claim 18, wherein said processor quantizes said e(t) into one of at least two ranges, and selects a value for said Kp, Ki, and Kd as a function of a quantized one of said ranges.

21. The system of claim 18, further including means for replacing said output power control signal with a maximum power, based on said error signal.

22. A computer readable medium comprising:
software for execution by a computer processor to control a power output to a probe having a probe thermal element and a probe temperature sensor, and
a memory including at least one set of settings for said probe including at least one gain parameter and corresponding predetermined operating characteristics for said probe,
said software carrying out the following
(a) receiving said target probe temperature;
(b) receiving a first probe setting corresponding to a desired set of operating characteristics for said probe;
(c) selecting from said at least one set of probe settings a set of settings in response to said first probe setting;
(d) generating an error signal e(t) from a comparison of a sensed temperature sensed by said sensor and said target temperature;
(e) providing a control function for generating an output power control signal, said control function comprising a first mode wherein said output power control signal comprises a constant power, and a second mode wherein said output power control signal is generated based on an examination of a rate at which said sensed temperature approaches said target temperature and a determination of whether said sensed temperature will attain but not exceed said target temperature;
(f) using said error signal e(t) to dynamically control at least one factor of said control function to determine said output power control signal; and
(g) controlling power output to said thermal element responsive to said power output control signal.

23. The computer readable medium of claim 22, wherein said second mode is defined in part by:

$$Pout=Kp \cdot P+Ki \cdot I+Kd \cdot D$$

where Pout is said output power control signal, Kp is a proportional gain factor associated with said control function, Ki is an integral gain factor associated with said control function, Kd is a derivative gain factor associated with said control function, and P, I, and D are proportion, integration, and derivation functions associated with said control function.

24. The computer readable medium of claim 22, wherein using said error signal e(t) comprises quantizing said e(t) into one of at least two ranges, and selecting at least two of said Kp, Ki, and Kd as a function of a quantized one of said ranges.

25. The computer readable medium of claim 22, wherein said first mode comprises overriding said output power control signal with said maximum power.

26. The computer readable medium of claim 22, wherein using said error signal e(t) comprises limiting said output control signal to a predetermined output value when said output control signal exceeds a predetermined threshold.

27. A method comprising:
receiving a gain factor corresponding to an electrosurgical instrument;
receiving a target temperature;
receiving a sensed temperature; and
generating a power signal from a control function operating on the target temperature, the sensed temperature, and the gain factor.

28. The method of claim 27, further comprising generating an error signal based on a comparison of the sensed temperature with the target temperature.

29. The method of claim 28, wherein the gain factor comprises a proportional gain factor and generating the power signal comprises generating a proportional signal based on a product of the error signal and the proportional gain factor.

30. The method of claim 28, wherein generating the power signal comprises generating an integral signal based on an integral of the error signal.

31. The method of claim 30, wherein the gain factor comprises a proportional gain factor and generating the power signal comprises generating a proportional signal based on a product of the error signal and the proportional gain factor and combining the proportional signal and the integral signal.

32. The method of claim 28, wherein generating the power signal comprises generating a derivative signal based on a derivative of at least one of the error signal and the sensed temperature.

33. The method of claim 32, wherein the gain factor comprises a proportional gain factor and generating the power signal comprises generating a proportional signal based on a product of the error signal and the proportional gain factor, generating an integral signal based on an integral of the error signal, and combining the proportional signal, the integral signal, and the derivative signal.

34. The method of claim 32, wherein the gain factor comprises a proportional gain factor and generating the power signal comprises generating a proportional signal based on a product of the error signal and the proportional gain factor and combining the proportional signal and the derivative signal.

35. The method of claim 28, wherein the gain factor comprises a derivative gain factor and generating the power signal further comprises generating a derivative signal based on a product of the derivative gain factor and a derivative of at least one of the error signal and the sensed temperature.

36. The method of claim 35, wherein generating the power signal comprises generating an integral signal based on an integral of the error signal and combining the derivative signal and the integral signal.

37. The method of claim 28, wherein the gain factor comprises an integral gain factor and generating the power signal comprises generating an integral signal based on a product of the integral gain factor and an integral of the error signal.

38. The method of claim 27, wherein generating the power signal comprises generating an intermediate output signal, the power signal being limited to a predetermined maximum output value when the intermediate output signal exceeds a predetermined threshold value.

39. The method of claim 38, wherein generating the power signal comprises generating an antiwindup adjustment signal based on a comparison of the intermediate output signal and the power signal.

40. The method of claim 39, wherein generating the power signal comprises generating an error signal based on a comparison of the sensed temperature and the target temperature, generating a modified error signal based on a comparison of the antiwindup adjustment signal and the error signal, and generating an integral signal based on an integral of the modified error signal.

41. The method of claim 27, wherein receiving a gain factor comprises choosing the gain factor from one or more electrosurgical instrument gain factors.

42. The method of claim 27, further comprising providing the power signal to the electrosurgical instrument.

43. A method comprising:
choosing proportional, derivative, and integral gain factors corresponding to an electrosurgical instrument;
receiving a target temperature;
receiving a sensed temperature;
generating an error signal based on a comparison of the sensed temperature with the target temperature;
generating a power signal from a control function operating on a proportional signal based on a product of the error signal and the proportional gain factor, a derivative signal based on a product of the derivative gain factor and a derivative of at least one of the error signal and the sensed temperature, and an integral signal based on a product of the integral gain factor and an integral of the error signal; and
providing the power signal to the electrosurgical instrument.

44. The method of claim 43, wherein generating the power signal comprises generating an intermediate output signal, the power signal being limited to a predetermined maximum output value when the intermediate output signal exceeds a predetermined threshold value.

45. A method comprising:
receiving a target temperature;
receiving a sensed temperature;
generating an error signal based on a comparison of the sensed temperature and the target temperature;
receiving a parameter for a control function for generating a power signal for an electrosurgical instrument; and
replacing the parameter for the control function with a second parameter for the control function based on a comparison of the error signal and a threshold value.

46. The method of claim 45, further comprising generating the power signal for the electrosurgical instrument by executing the control function.

47. The method of claim 46, wherein the parameter comprises a gain factor and generating the power signal comprises generating a proportional signal based on a product of the error signal and the gain factor.

48. The method of claim 46, wherein the parameter comprises a gain factor and generating the power signal comprises generating an integral signal based on a product of the gain factor and an integral of the error signal.

49. The method of claim 46, wherein the parameter comprises a gain factor and generating the power signal comprises generating a derivative signal based on a product of the gain factor and a derivative of at least one of the error signal and the sensed temperature.

50. The method of claim 45, further comprising switching the power signal to a maximum power based on a comparison of the error signal and a maximum power threshold value.

51. The method of claim 50, wherein the power signal is switched to the maximum power when the error signal is greater than the maximum power threshold value.

52. The method of claim 50, wherein the power signal is switched to the maximum power when the error signal is equal to the maximum power threshold value.

53. The method of claim 45, wherein the threshold value comprises a measured value.

54. The method of claim 53, wherein the measured value is selected from the group consisting of a temperature value, an impedance value, and a voltage value.

55. The method of claim 45, wherein receiving the parameter comprises choosing the parameter for the control function from among multiple parameters.

56. The method of claim 55, wherein replacing the parameter for the control function with the second parameter for the control function comprises choosing the second parameter from among multiple parameters.

57. The method of claim 45, wherein receiving the parameter comprises choosing the parameter based on a comparison of the error signal and a second threshold value.

58. The method of claim 45, wherein the parameter comprises a gain factor, and receiving the parameter comprises receiving the gain factor.

59. A method comprising:
receiving a target temperature;
receiving a sensed temperature;
generating an error signal based on a comparison of the sensed temperature and the target temperature;
choosing proportional, integral, and derivative gain factors, based on a comparison of the error signal and a first threshold value;
replacing original gain factors in a control function for generating a power signal for an electrosurgical instrument with the proportional gain factor, the integral gain factor, and the derivative gain factor;
generating the power signal with the control function including generating a proportional signal based on a product of the error signal and the proportional gain factor, generating an integral signal based on a product of the integral gain factor and an integral of the error signal, generating a derivative signal based on a product of the derivative gain factor and a derivative of at least one of the error signal and the sensed temperature, and combining the proportional signal, the integral signal and the derivative signal; and
switching the power signal to a maximum power based on a comparison of the error signal and a second threshold value.

60. A device comprising:
means for receiving a target temperature;
means for receiving a sensed temperature;
means for generating an error signal based on a comparison of the sensed temperature and the target temperature;
means for receiving a parameter for a control function for generating a power signal for an electrosurgical instrument and
means for replacing the parameter for the control function with a second parameter for the control function based on a comparison of the error signal and a threshold value.

61. The device of claim 60, further comprising means for generating the power signal for the electrosurgical instrument by executing the control function.

62. The device of claim 61, wherein the parameter comprises a gain factor and the means for generating the power signal comprises means for generating a proportional signal based on a product of the error signal and the gain factor.

63. The device of claim 61, wherein the parameter comprises a gain factor and the means for generating the power signal comprises means for generating an integral signal based on a product of the gain factor and an integral of the error signal.

64. The device of claim 61, wherein the parameter comprises a gain factor and the means for generating the power signal comprises means for generating a derivative signal based on a product of the gain factor and a derivative of at least one of the error signal and the sensed temperature.

65. The device of claim 60, further comprising means for switching the power signal to a maximum power based on a comparison of the error signal and a maximum power threshold value.

66. The device of claim 65, wherein the power signal is switched to the maximum power when the error signal is greater than the maximum power threshold value.

67. The device of claim 65, wherein the power signal is switched to the maximum power when the error signal is equal to the maximum power threshold value.

68. The device of claim 60, wherein the threshold value comprises a measured value.

69. The device of claim 68, wherein the measured value is selected from the group consisting of a temperature value, an impedance value, and a voltage value.

70. The device of claim 60, wherein the means for receiving the parameter comprises means for choosing the parameter for the control function from among multiple parameters.

71. The device of claim 70, wherein the means for replacing the parameter for the control function with the second parameter for the control function comprises means for choosing the second parameter from among multiple parameters.

72. The device of claim 60, wherein the means for receiving the parameter comprises means for choosing the parameter based on a comparison of the error signal and a second threshold value.

73. The method of claim 60, wherein the parameter comprises a gain factor, and the means for receiving the parameter comprises means for receiving the gain factor.

74. A device comprising:
means for receiving a target temperature;
means for receiving a sensed temperature;
means for generating an error signal based on a comparison of the sensed temperature and the target temperature;
means for choosing proportional, integral, and derivative gain factors, based on a comparison of the error signal and a first threshold value;
means for replacing original gain factors in a control function for generating a power signal for an electrosurgical instrument with the proportional gain factor, the integral gain factor, and the derivative gain factor;
means for generating the power signal with the control function comprising means for generating a proportional signal based on a product of the error signal and the proportional gain factor, means for generating an integral signal based on a product of the integral gain factor and an integral of the error signal, means for generating a derivative signal based on a product of the derivative gain factor and a derivative of at least one of the error signal and the sensed temperature, and means for combining the proportional signal, the integral signal and the derivative signal; and
means for switching the power signal to a maximum power based on a comparison of the error signal and a second threshold value.

75. A device comprising:
a first input component configured to receive a sensed temperature;
a second input component configured to receive a target temperature;
a third input component configured to receive a gain factor corresponding to an electrosurgical instrument;
a power control circuit coupled to the first input component, the second input component, and the third input component, the power control circuit operable on the sensed temperature, the target temperature, and the gain factor and configured to generate a power signal for the electrosurgical instrument.

76. The device of claim 75, wherein the power control circuit comprises a summing component configured to generate an error signal based on a difference between the sensed temperature and the target temperature.

77. The device of claim 76, wherein the gain factor comprises a proportional gain factor and the power control circuit further comprises an amplifier component configured to multiply the proportional gain factor and the error signal to generate a proportional signal.

78. The device of claim 76, wherein the gain factor comprises a derivative gain factor and the power control circuit further comprises a derivative component configured to take a derivative of the error signal to generate an intermediate signal and an amplifier component configured to multiply the intermediate signal and the derivative gain factor to generate a derivative signal.

79. The device of claim 76, wherein the gain factor comprises an integral gain factor and the power control circuit further comprises an integrator component configured to integrate the error function to generated an intermediate signal and an amplifier configured to multiply the intermediate signal and the integral gain factor to generate an integral signal.

80. The device of claim 75, wherein the gain factor comprises a derivative gain factor and the power control circuit further comprises a derivative component configured to take a derivative of the sensed temperature to generate an intermediate signal and an amplifier component configured to multiply the intermediate signal and the derivative gain factor to generate a derivative signal.

81. The device of claim 75, further comprising a memory containing multiple electrosurgical instrument gain factors and a selector configured to select the gain factor from among the multiple electrosurgical instrument gain factors.

82. A device comprising:
a first input component configured to receive a sensed temperature;
a second input component configured to receive a target temperature;
a power control circuit coupled to the first input component and the second input component, the power control circuit operable on the sensed temperature, the target temperature, and a parameter and configured to generate a power signal for an electrosurgical instrument, the power control circuit comprising (i) a summing component configured to generate an error signal based on a difference between the sensed temperature and the target temperature, and (ii) a selector component configured to choose the parameter for the control function and configured to replace the parameter for the control function with a second parameter for the control function based on a comparison of the error signal and a threshold value.

* * * * *

UNITED STATES PATENT AND TRADEMARK OFFICE
CERTIFICATE OF CORRECTION

PATENT NO. : 6,939,346 B2  Page 1 of 1
APPLICATION NO. : 10/187462
DATED : September 6, 2005
INVENTOR(S) : Donald P. Kannenberg and Duane W. Marion It is certified that error appears in the above-identified patent and that said Letters Patent is hereby corrected as shown below:

Column 1:
Line 1, insert --co-pending-- between "applicant's" and "U.S.".
Line 63, replace "delivery" with --deliver--.

Column 6:
Line 9, delete "-" between "probe" and "temperature"
Line 16, delete ")" after "SETTINGS".

Column 23:
Line 16, replace "generated" with --generate--.

Signed and Sealed this

Fifth Day of September, 2006

JON W. DUDAS
*Director of the United States Patent and Trademark Office*